United States Patent
Fairbanks et al.

(10) Patent No.: US 8,231,688 B2
(45) Date of Patent: Jul. 31, 2012

(54) SEMI-ACTUATED TRANSFEMORAL PROSTHETIC KNEE

(75) Inventors: Dylan Miller Fairbanks, Oakland, CA (US); Adam Brian Zoss, Berkeley, CA (US); Minerva Vasudevan Pillai, Lafayette, CA (US); Miclas Schwartz, Hamburg (DE); Nathan Harding, Oakland, CA (US); Matthew Rosa, San Francisco, CA (US); Bram Gilbert Antoon Lambrecht, Berkeley, CA (US); Sebastian Kruse, Berkeley, CA (US); Homayoon Kazerooni, Berkeley, CA (US)

(73) Assignees: Berkeley Bionics, Berkeley, CA (US); The Regents of the University of California, Oakland, CA (US)

( * ) Notice: Subject to any disclaimer, the term of this patent is extended or adjusted under 35 U.S.C. 154(b) by 133 days.

(21) Appl. No.: 12/457,573

(22) Filed: Jun. 16, 2009

(65) Prior Publication Data
US 2010/0023133 A1 Jan. 28, 2010

Related U.S. Application Data

(60) Provisional application No. 61/132,217, filed on Jun. 16, 2008, provisional application No. 61/136,535, filed on Sep. 12, 2008.

(51) Int. Cl.
*A61F 2/48* (2006.01)
*A61F 2/60* (2006.01)
*A61F 2/68* (2006.01)
(52) U.S. Cl. ............... 623/27; 623/24; 623/26; 623/44
(58) Field of Classification Search ............ 623/27, 623/35–46, 24, 26
See application file for complete search history.

(56) References Cited

U.S. PATENT DOCUMENTS

| | | | |
|---|---|---|---|
| 3,863,274 | A | 2/1975 | Glabiszewski |
| 5,062,856 | A | 11/1991 | Sawamura et al. |
| 5,344,446 | A | 9/1994 | Sawamura et al. |

(Continued)

FOREIGN PATENT DOCUMENTS

WO 2007/016781 2/2007

(Continued)

OTHER PUBLICATIONS

Flowers, "A Man-Interactive Simulator System", Ph.D. Thesis, Massachusetts Institute of Technology, 1972.

(Continued)

*Primary Examiner* — Thomas J Sweet
*Assistant Examiner* — Marcia Hoffman
(74) *Attorney, Agent, or Firm* — Diederiks & Whitelaw, PLC

(57) ABSTRACT

A semi-actuated above knee prosthetic system, which is mostly passive in nature and includes a shank link coupled to an artificial foot, a knee mechanism connected to the shank link and a thigh link attached to an above-knee remaining lower limb of an amputee, is operable in either an actuated mode or an un-actuated mode controlled by a signal processor linked to various prosthetic mounted sensors which may include combinations of knee angle, stance, thigh angle and shank angle sensors. Power is delivered through an electric motor connected to a battery source and employed to drive a hydraulic pump which is part of an overall hydraulic power unit including the torque generator. A signal processor selects a swing state from at least forward, combination forward and descent, combination forward and ascent, reverse, combination reverse and descent, and combination reverse and ascent swing states.

48 Claims, 33 Drawing Sheets

U.S. PATENT DOCUMENTS

| | | | |
|---|---|---|---|
| 5,383,939 A | 1/1995 | James | |
| 5,405,409 A | 4/1995 | Knoth | |
| 5,443,521 A | 8/1995 | Knoth et al. | |
| 5,571,205 A | 11/1996 | James | |
| 5,704,945 A | 1/1998 | Wagner et al. | |
| 5,755,813 A | 5/1998 | Krukenberg | |
| 5,888,212 A | 3/1999 | Petrofsky et al. | |
| 5,893,891 A | 4/1999 | Zahedi | |
| 5,899,869 A * | 5/1999 | Barrack et al. | 602/16 |
| 6,113,642 A | 9/2000 | Petrofsky et al. | |
| 6,517,585 B1 | 2/2003 | Zahedi et al. | |
| 6,610,101 B2 | 8/2003 | Herr et al. | |
| 6,719,806 B1 | 4/2004 | Zahedi et al. | |
| 6,755,870 B1 | 6/2004 | Biedermann et al. | |
| 6,764,520 B2 | 7/2004 | Deffenbaugh et al. | |
| 7,198,071 B2 | 4/2007 | Bisbee, III et al. | |
| 7,279,009 B2 | 10/2007 | Herr et al. | |
| 7,314,490 B2 | 1/2008 | Bedard et al. | |
| 7,883,546 B2 * | 2/2011 | Kazerooni et al. | 623/27 |
| 2004/0181289 A1 | 9/2004 | Bedard et al. | |
| 2006/0235544 A1 | 10/2006 | Iversen et al. | |
| 2006/0249315 A1 | 11/2006 | Herr et al. | |
| 2006/0293761 A1 | 12/2006 | Baumann et al. | |
| 2007/0016329 A1 | 1/2007 | Herr et al. | |
| 2007/0043449 A1 | 2/2007 | Herr et al. | |
| 2007/0050044 A1 | 3/2007 | Haynes et al. | |
| 2007/0056592 A1 | 3/2007 | Angold et al. | |
| 2007/0233279 A1 | 10/2007 | Kazerooni et al. | |

FOREIGN PATENT DOCUMENTS

| | | |
|---|---|---|
| WO | 2007/025116 | 3/2007 |

OTHER PUBLICATIONS

Riener et al., "Stair Ascent and Descent at Different Inclinations", Gait and Posture, No. 15, pp. 32-44, 2002.

Au et al., "Powered Ankle-Foot Prosthesis for the Improvement of Amputee Ambulation", Proc. of the $29^{th}$ Annual International Conf. of the IEEE EMBS, Lyon, France, pp. 3020-3026, 2007.

Lambrecht, "Design of a Hybrid Passive-Active Prosthesis for Above-Knee Amputees", Ph.D. Thesis, University of California at Berkeley, 2008.

Sup et al, "Design and Control of a Powered Transfemoral Prosthesis", International Journal of Robotics Research, No. 27; 263, 2008.

Lambrecht et al, "Design of a Seim-Active Knee Prosthesis", 2009 IEEE International Conference on Robotics and Automation, Kobe, JP, pp. 639-645, 2009.

Sup et al., "Design and Control of a Powered Knee and Ankle Prosthesis", 2007 IEEE International Conference on Robotics and Automation Roma, Italy, pp. 4134-4139, 2007.

Kapti et al., "Design and Control of an Active Artificial Knee Joint", Mechanism and Machine Theory, No. 41, pp. 1477-1485, 2006.

Popovic et al., "Optimal Control for an Above-Knee Prosthesis with Two Degrees of Freedom", Journal of BioMechanics, vol. 28, No. 1, pp. 89-98, 1995.

Horn, "Electro-Control: am EMG-Controlled A/K Prosthesis", Med. & Biol. Eng., vol. 10, pp. 61-73, 1972.

Bionic Technology by Ossur, "Technical Manual, Proprio Foot", 2009.

* cited by examiner

SEMI-ACTUATED TRANSFEMORAL PROSTHETIC KNEE

CROSS-REFERENCE TO RELATED APPLICATIONS

This application claims the benefit of U.S. Provisional Application No. 61/132,217 entitled SEMI-ACTUATED TRANSFEMORAL PROSTHETIC KNEE, filed on filed Jun. 16, 2008, and U.S. Provisional Application 61/136,535 entitled SEMI-ACTUATED TRANSFEMORAL PROSTHETIC KNEE, filed Sep. 12, 2008.

STATEMENT REGARDING FEDERALLY SPONSORED RESEARCH OR DEVELOPMENT

This invention was made with government support under Award No. W81XWH-05-C-0147 awarded by Telemedicine & Advanced Technology Research Center, Department of the Army and under Award No. CMS-0510848 awarded by the National Science Foundation. The government has certain rights in the invention.

BACKGROUND OF THE INVENTION

The present invention relates generally to the field of prosthetics and, more specifically, to controlling powered and non-powered operations of a prosthetic attached to an above-knee remaining lower limb of an amputee.

In recent years, major advancements have been made in the field of prosthetics. For instance, not only are prosthetics now commonly available for customized fit in connection with a wide range of amputations, but the prosthetics themselves can be customized for use as well. Therefore, fitting an amputee with a prosthetic includes not only customization for size, but also variations based on various other factors, particularly the types of activities in which the amputee will be utilizing the prosthetic device.

In connection with above-knee prosthetics, both swing and stance controls must be established. Certainly, swing controls have to accommodate for a greater range of motions, with the potential motions even varying in dependence on the age and activity level of the amputee. In this regard, fluid systems have been employed in the past, often due to their ability to establish relatively consistent motions. However, fluctuations in the speed of movement may be needed as well such that proper control of the fluid system is also needed.

SUMMARY OF THE INVENTION

The present invention is concerned with a semi-actuated above knee prosthetic system that is mostly passive in nature in that the system only requires power for locomotion during a portion of a walking cycle. In general, the prosthetic includes a shank link adapted to be coupled to an artificial foot, a knee mechanism connected to the shank link at a position remote from the artificial foot and a thigh link adapted to be attached to an above-knee remaining lower limb of an amputee. The knee mechanism is configured to provide flexion and extension movements of the thigh and shank links relative to each other. In accordance with the invention, the prosthetic is operable in either an actuated mode or an un-actuated mode. In the actuated mode, power is delivered to a torque generator connected to the knee mechanism to cause a forced movement between the thigh and shank links. In the un-actuated mode, a control circuit operates in a non-powered manner to allow operation of the knee mechanism with modulated resistance.

In accordance with a preferred embodiment of the invention, an electric motor is connected to a battery source and employed to drive a hydraulic pump which is part of an overall hydraulic power unit including the torque generator used to regulate the knee mechanism. A signal processor controls the operation of the hydraulic power unit in order to establish the actuated and un-actuated modes based on signals received from a plurality of sensors provided on the above-knee prosthetic. Although the location, number and type of sensors can vary, one preferred embodiment employs a stance sensor capable of identifying a particular part of an artificial foot which is in contact with a support surface (e.g., the ground), while the signal processor selects a desired swing state when the artificial foot leaves the support surface based on an estimated location of the artificial foot with respect to a trunk of the amputee. Knee angle, thigh angle, pressure and other sensors can also be employed for additional control purposes.

With this arrangement, the overall system advantageously employs less electric power than fully powered knees and therefore an amputee can walk much longer for a given battery size. In addition, the above-knee prosthetic of the invention is generally smaller than fully actuated knees. Furthermore, the semi-actuated prosthetic knee reduces necessary hip torque and power that the amputee must physically exert by efficiently creating synchronized torque and power during an effective portion of a walking cycle. Even further, the various sensors provide inputs to the signal processor that effectively maximize the range and type of motions generated for the amputee.

Additional objects, features and advantages of the invention will become more fully evident below from the following detailed description of preferred embodiments wherein like reference numerals refer to corresponding parts in the various views.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
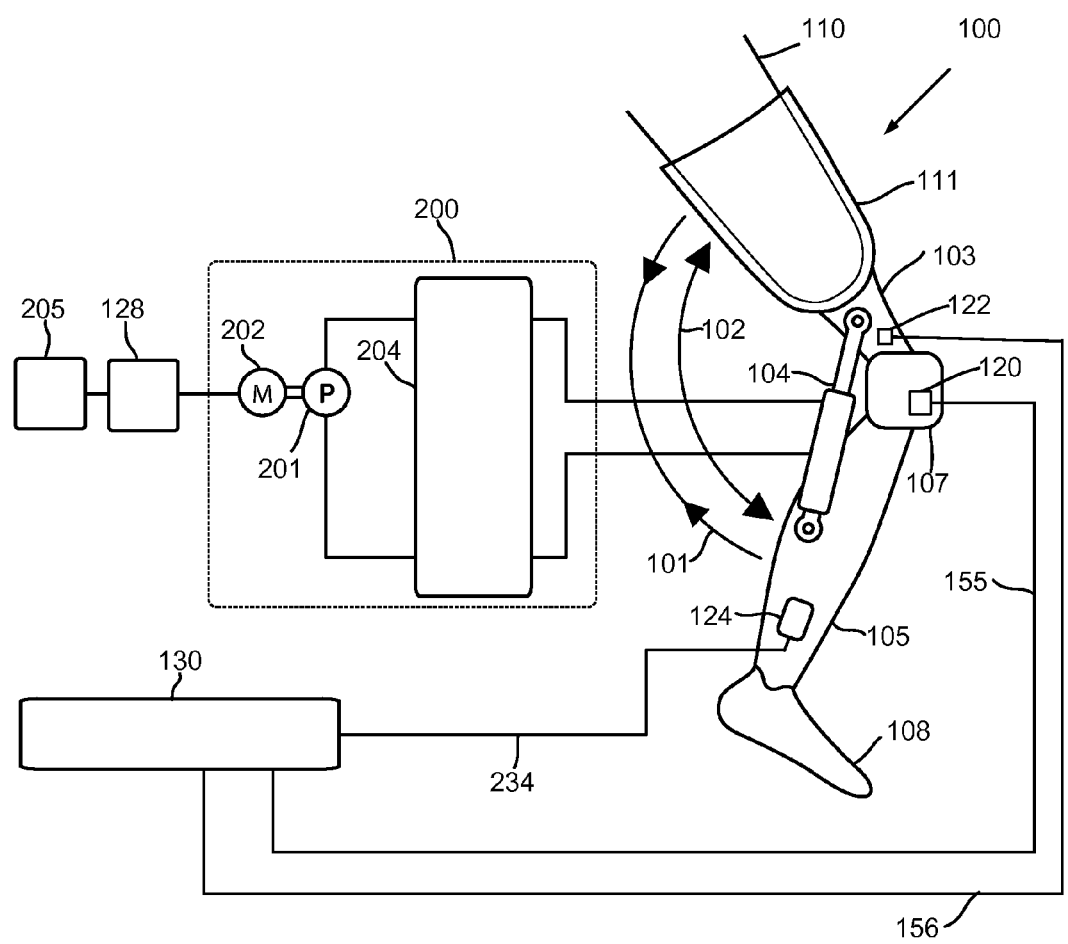
FIG. 1 depicts a semi-actuated prosthetic knee constructed in accordance with a first embodiment of the invention.

With initial reference to FIG. 1, a semi-actuated prosthetic knee 100 constructed in accordance with a first embodiment of the invention is configurable to be coupled to an above-knee amputee's remaining lower limb 110 through a socket 111. Semi-actuated prosthetic knee 100, among other components, comprises a thigh link 103 coupled to a knee mechanism 107 and a shank link 105 coupled to an artificial foot 108. Knee mechanism 107 is configured to allow flexion and extension movements of thigh link 103 and a shank link 105 relative to each other along flexion direction 101 and extension direction 102. A hydraulic torque generator 104 is configured to generate torque between thigh link 103 and shank link 105.

Semi-actuated prosthetic knee 100 further includes a hydraulic power unit indicated at 200 coupled to hydraulic torque generator 104. Hydraulic power unit 200, among other components, includes a hydraulic valve circuit 204, which is hydraulically coupled to torque generator 104. Hydraulic power unit 200 further includes a hydraulic pump 201 mechanically coupled to an electric motor 202 and hydraulically coupled to hydraulic valve circuit 204.

Semi-actuated prosthetic knee 100 further includes an electric power source 205 capable of providing electric power to electric motor 202 and other components of semi-actuated prosthetic knee 100. A motor controller 128 (sometimes referred to as an amplifier) converts the output of electric power source 205 to an appropriate voltage or current for electric motor 202. Semi-actuated prosthetic knee 100 further includes a signal processor 130 that among other tasks controls electric motor 202 and implements a controller that includes a set of states. Semi-actuated prosthetic knee 100 additionally includes a stance sensor 124 producing stance signal 234. Stance signal 234, among other information, includes information identifying which part of artificial foot 108 is in contact with the ground.

In operation when semi-actuated prosthetic knee 100 is in its actuated mode, semi-actuated prosthetic knee 100 is configured such that it transfers electric power from electric power source 205 to electric motor 202, powering electric motor 202 and hydraulic pump 201. In this actuated mode, hydraulic valve circuit 204 is configured such that hydraulic pump 201 hydraulically couples to torque generator 104. This hydraulic coupling between hydraulic pump 201 and torque generator 104 allows signal processor 130 to control torque generator 104. The ability to inject power to torque generator 104 allows one to control the motion of knee mechanism 107 or impose desirable torque onto knee mechanism 107 during various phases of the walking cycle.

When semi-actuated prosthetic knee 100 is in an un-actuated mode, hydraulic power unit 200 is configured such that no electric power from electric power source 205 is transferred to electric motor 202. In this un-actuated mode hydraulic valve circuit 204 modulates the resistance of the fluid flow in torque generator 104. The ability to modulate the resistance of fluid flow in torque generator 104 allows one to control the resistance of knee mechanism 107 to forces and torques during various phases of the walking cycle with reduced use of electric power since electric motor 202 is not consuming any electric power in this un-actuated mode.

Examples of hydraulic torque generators 104 include, without limitation, linear hydraulic piston-cylinders, rotary hydraulic actuators, rack-and-pinion-type rotary actuators and rotary hydraulic vane type actuators where pressurized hydraulic fluid, by pushing against moving surfaces, generate force or torque.

Examples of electric power source 205 include, without limitation, batteries, Nickel-Metal Hydride (NiMH) batteries, Lithium batteries, Alkaline batteries, rechargeable Alkaline batteries, Lithium-ion batteries, and Lithium ion polymer batteries.

Examples of electric motor 202 include, without limitation, electric motors, including, without limitation, AC (alternating current) motors, brush-type DC (direct current) motors, brushless DC motors, electronically commutated motors (ECMs), stepping motors, and combinations thereof.

Examples of hydraulic pump 201 include, without limitation, gear pumps, gerotor pumps, rotary vane pumps, screw pumps, bent axis pumps, axial piston pumps swashplate pumps, radial piston pumps, and peristaltic pumps.

Examples of stance sensor 124 include, without limitation, force sensors, strain gage force sensors, piezoelectric force sensors, force sensing resistors, load cells, deflection-based positioning sensors, encoders, potentiometers, pressure sensors in a trapped hydraulic fluid, and combinations thereof.

Examples of knee mechanism 107 include, without limitation, rotary pivots, four-bar linkages sliding joints, rolling element joints, and combinations thereof.

Signal processor 130 comprises an element or combination of elements selected from the group consisting of analog devices; analog computation modules; digital devices including, without limitation, small-, medium-, and large-scale integrated circuits, application specific integrated circuits, programmable gate arrays, programmable logic arrays; electromechanical relays, solid state switches, MOSFET switches and digital computation modules including, without limitation, microcomputers, microprocessors, microcontrollers, and programmable logic controllers. In operation signal processor 130 collects information from various sensors and after some computation commands what various components of hydraulic circuit should do.

In some embodiments of the invention, as shown in FIG. 1, semi-actuated prosthetic knee 100 further comprises a knee angle sensor 120 which generates a knee angle signal indicated at 155 representing the angle between thigh link 103 and shank link 105. Knee angle sensor 120 comprises an element or combination of elements selected from the group consisting of an encoder, digital encoder, magnetic encoder, optical encoder, potentiometer, LVDT, and resolver.

Figure 22:
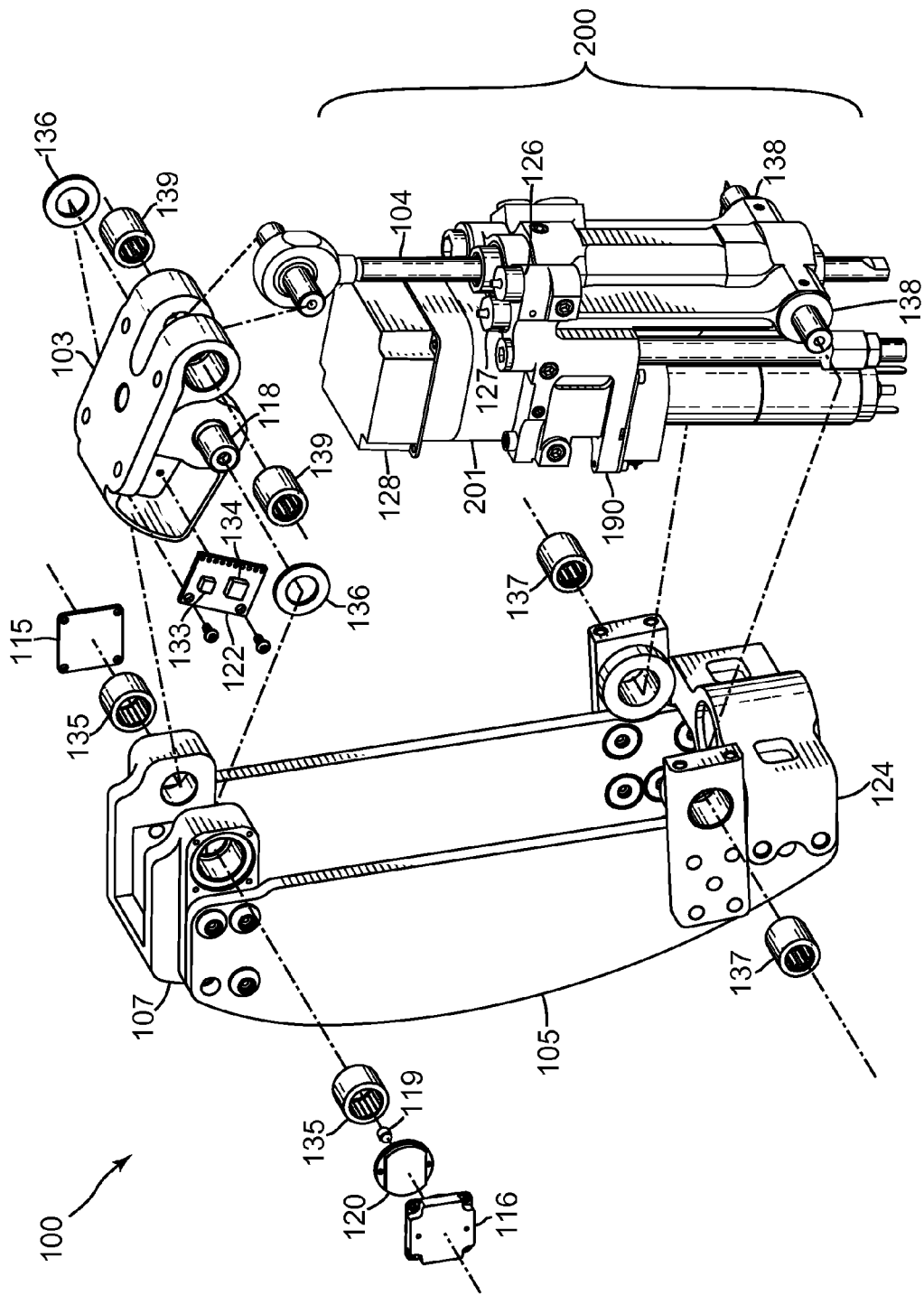
FIG. 22 is an exploded view of the semi-actuated prosthetic knee of FIG. 21.

In some embodiments, as shown in FIG. 1, semi-actuated prosthetic knee 100 further comprises a thigh angle sensor 122, which generates a thigh angle signal indicated at 156 representing the absolute angle of thigh link 103. Thigh angle sensor 122 comprises an element or combination of elements selected from the group consisting of, accelerometers, gyroscopes, inclinometers, encoders, potentiometers and combinations thereof FIG. 22 represents an embodiment of the invention where thigh angle sensor 122 fixed to thigh link 103 comprises an accelerometer 133 and a gyroscope 134.

Figure 16:
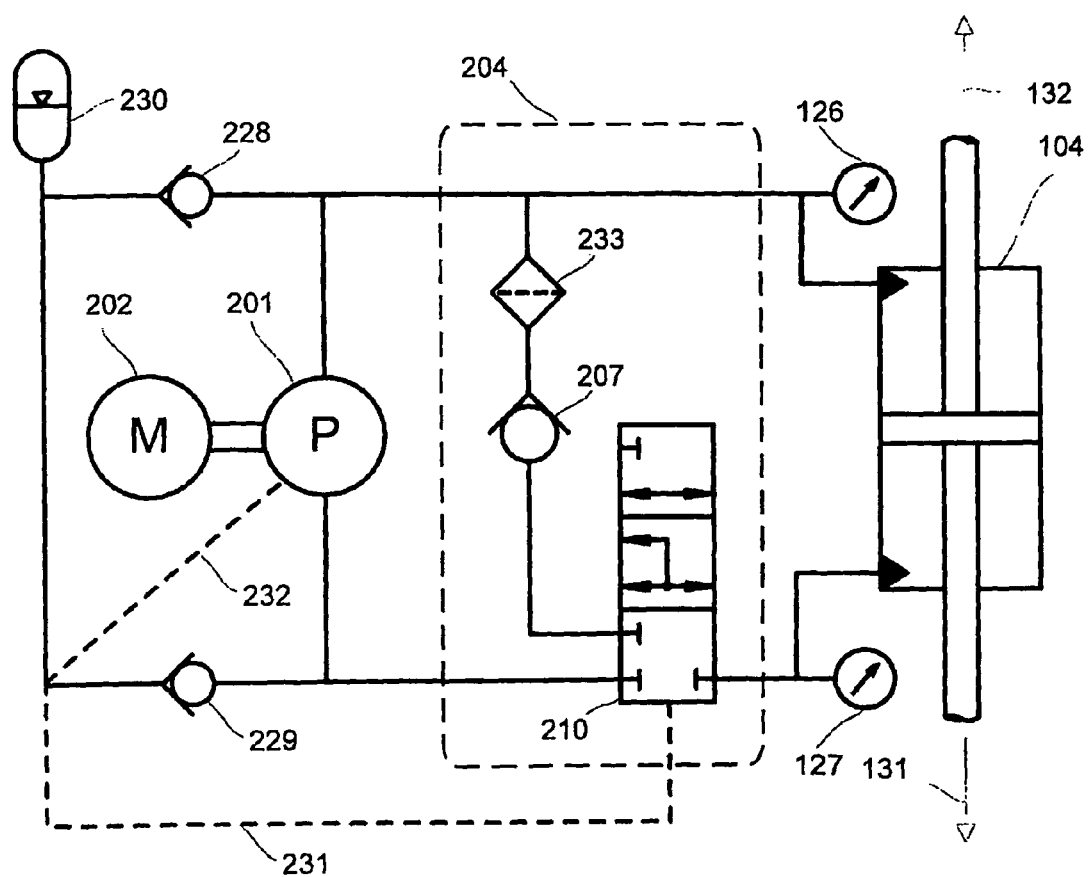
FIG. 16 is a diagram of an alternative hydraulic valve circuit including a fluid reservoir.

In some embodiments of the invention semi-actuated prosthetic knee 100 further comprises a torque sensor or a force sensor (as detailed below) representing the torque or force of torque generator 104. In some embodiments of the invention a force sensor is installed on the piston of linear torque generator 104. In some embodiments of the invention, the force sensor for semi-actuated prosthetic knee 100 comprises two pressure sensors 126 and 127 measuring the fluid pressure in both sides of torque generator 104, as depicted in FIG. 16. The measurements from two pressure sensors 126 and 127 also represent the force in torque generator torque generator 104.

In some embodiments as shown in FIG. 1, stance sensor 124 comprises a force-torque sensor installed on shank link 105 measuring the force and the moment in the sagittal plane.

Figure 2:
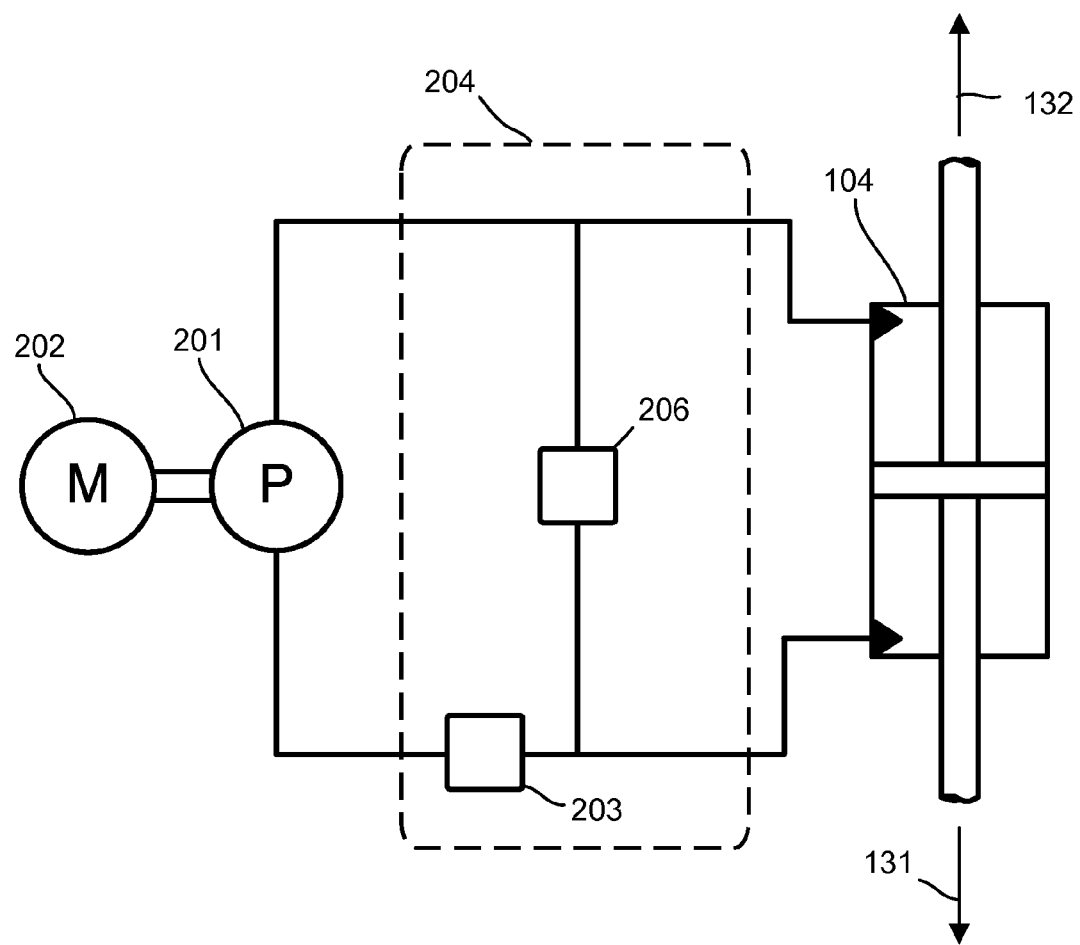
FIG. 2 is a diagram of a first hydraulic valve circuit of the present invention.

In some embodiments, as shown in FIG. 2, hydraulic valve circuit 204 comprises a first controllable valve 206 capable of allowing the hydraulic flow in two directions and a pump valve 203 serially connected to each other. Hydraulic pump 201 is coupled to two end ports of this serially-connected chain of first controllable valve 206 and pump valve 203. Torque generator 104 is coupled to two ports of first controllable valve 206. In some cases, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in the actuated mode, allows one to control the motion of knee mechanism 107 or impose desirable torque onto knee mechanism 107.

When semi-actuated prosthetic knee 100 operates in its un-actuated mode, pump valve 203 is either closed or partially closed. When pump valve 203 is fully closed, no flow passes through hydraulic pump 201. Through the use of signal processor 130, one can adjust the opening of first controllable valve 206 to modulate and adjust properly the resistance of fluid flow in torque generator 104. When pump valve 203 is partially closed, one can only modulate the resistance of fluid flow in torque generator 104 from zero to the combined flow resistance of pump valve 203 and hydraulic pump 201. The ability to modulate the resistance of fluid flow in torque generator 104 allows one to control the resistance of knee mechanism 107 to forces and torques with reduced use of electric power since electric motor 202 is not consuming any electric power in this un-actuated mode.

When semi-actuated prosthetic knee 100 operates in a power regenerative mode, pump valve 203 is not closed, allowing at least a portion of the hydraulic flow from torque generator 104 to turn hydraulic pump 201 while motor controller 128 applies a non-zero current onto electric motor 202 to resist the hydraulic flow in hydraulic pump 201.

For better clarification of the embodiments of hydraulic valve circuit 204, the flexion and extension will be defined as follows. The flexion of prosthetic knee 100 takes place when the piston of torque generator 104 moves in direction of arrow 131 depicted in FIG. 2. Extension of prosthetic knee 100 takes place when the piston of torque generator 104 moves in direction of arrow 132 depicted in FIG. 2.

Figure 3:
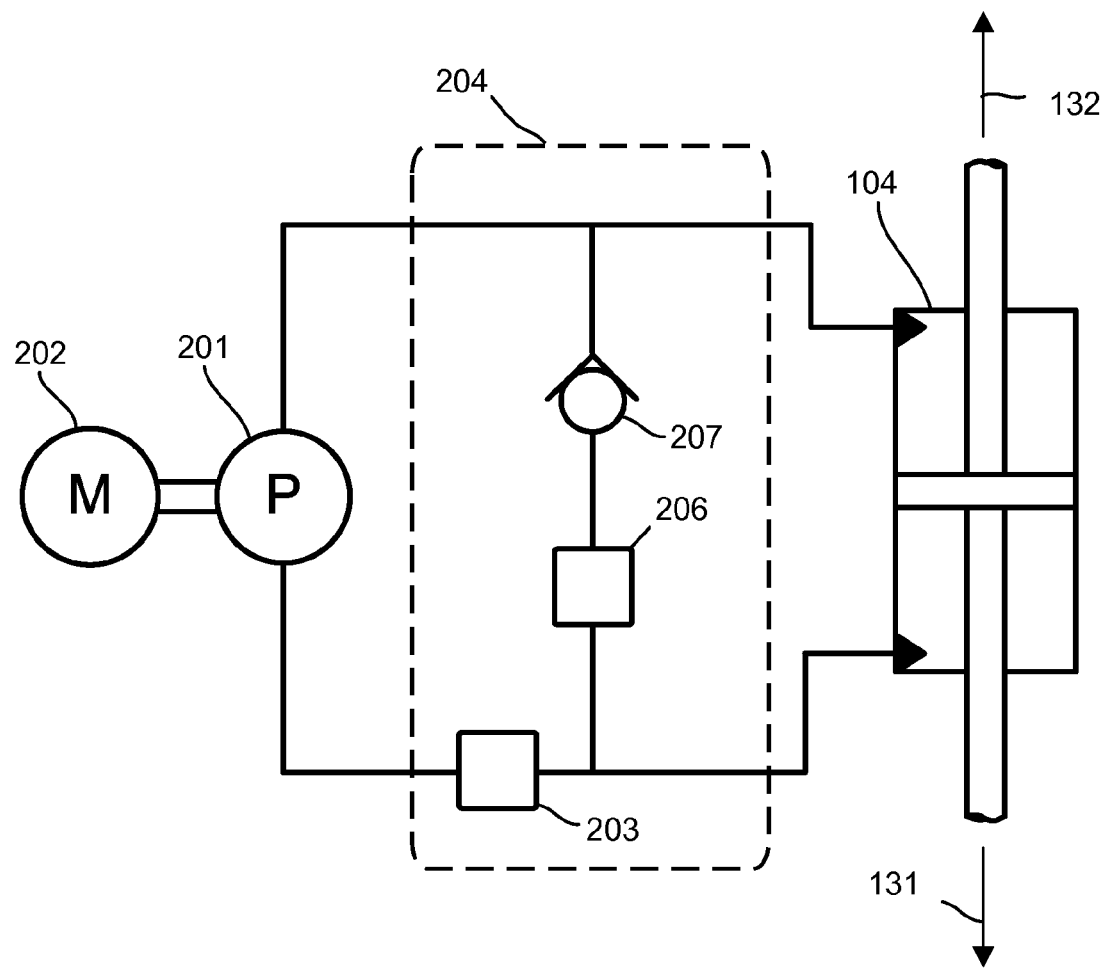
FIG. 3 is a diagram of the hydraulic valve circuit of FIG. 2, further comprising a first check valve.

In some embodiments, as shown in FIG. 3, hydraulic valve circuit 204, among other components, further comprises a first check valve 207 installed in series with first controllable valve 206. The operation of this embodiment is similar to the operation of the embodiment shown in FIG. 2, except that first hydraulic controllable valve 206 modulates the resistance of the fluid flow in torque generator 104 in one direction only. In comparison with the embodiment of FIG. 2, this embodiment constrains the range of resistance of fluid flow in torque generator 104 in flexion direction to always be more than the flow resistance that hydraulic pump 201 creates. It further allows free extension of torque generator 104 if first controllable valve 206 is open without compromising the ability to inject power in the extension direction of torque generator 104. Similar to the embodiment of FIG. 2, when semi-actuated prosthetic knee 100 operates in its actuated mode, first controllable valve 206 is closed. This allows signal processor 130 to control torque generator 104 by controlling electric motor 202. The ability to inject power to torque generator 104, in the actuated mode, allows one to control the motion of knee mechanism 107 or impose desirable torque onto knee mechanism 107.

Figure 4:
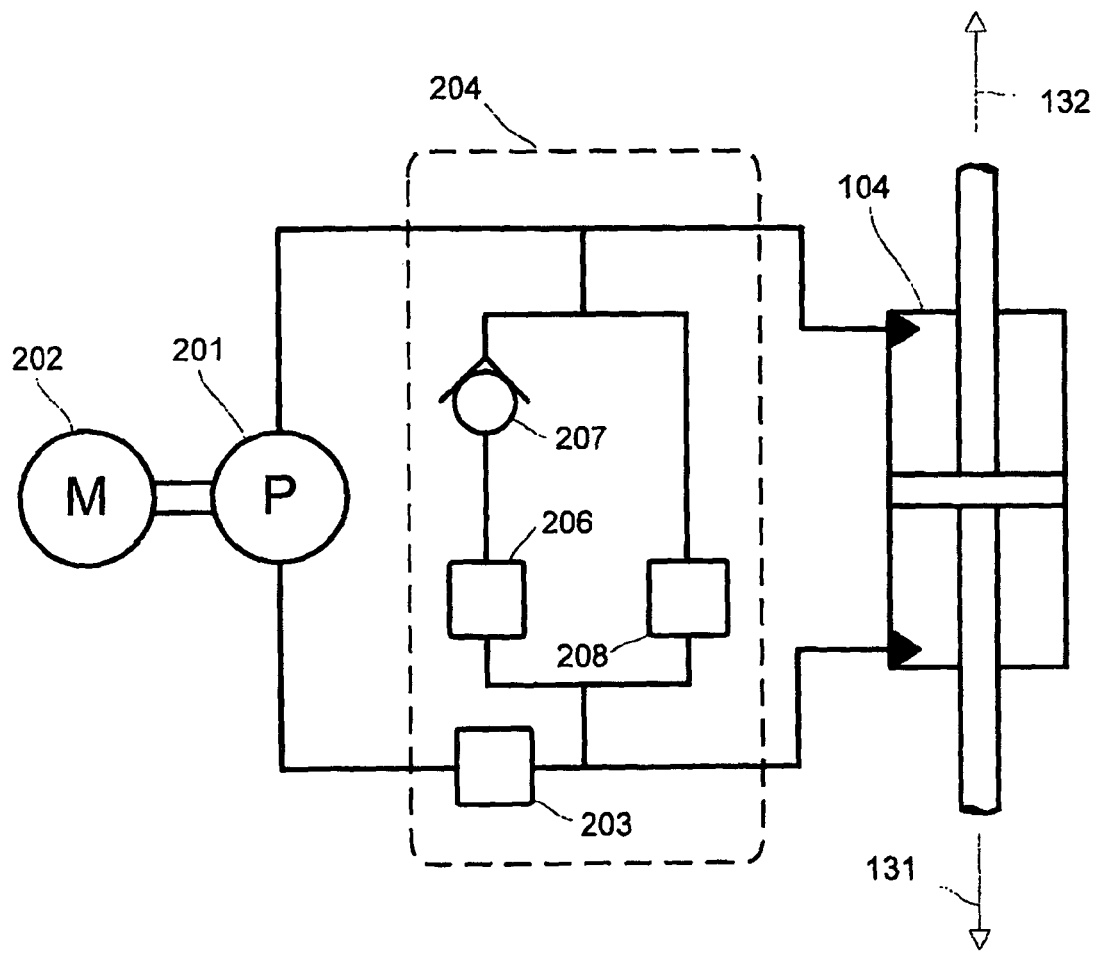
FIG. 4 is a diagram of the hydraulic valve circuit of FIG. 3, further comprising a second controllable valve.

In some embodiments, as shown in FIG. 4, hydraulic valve circuit 204, among other components, further comprises a second controllable valve 208 installed in parallel with serially-installed first controllable valve 206 and first check valve 207. Through the use of signal processor 130, one can adjust the opening of first controllable valve 206 and second controllable valve 208 to modulate and adjust properly the resistance of fluid flow in torque generator 104. The operation of this embodiment is similar to the operation of the embodiment shown in FIG. 3, except that this embodiment does not constrain the range of resistance of fluid flow in flexion direction in torque generator 104. When semi-actuated prosthetic knee 100 operates in its actuated mode, first controllable valve 206 and second controllable valve 208 are closed. This allows signal processor 130 to control torque generator 104 by controlling electric motor 202. The ability to inject power to torque generator 104, in the actuated mode, allows one to control the motion of knee mechanism 107 or impose desirable torque onto knee mechanism 107.

Figure 5:
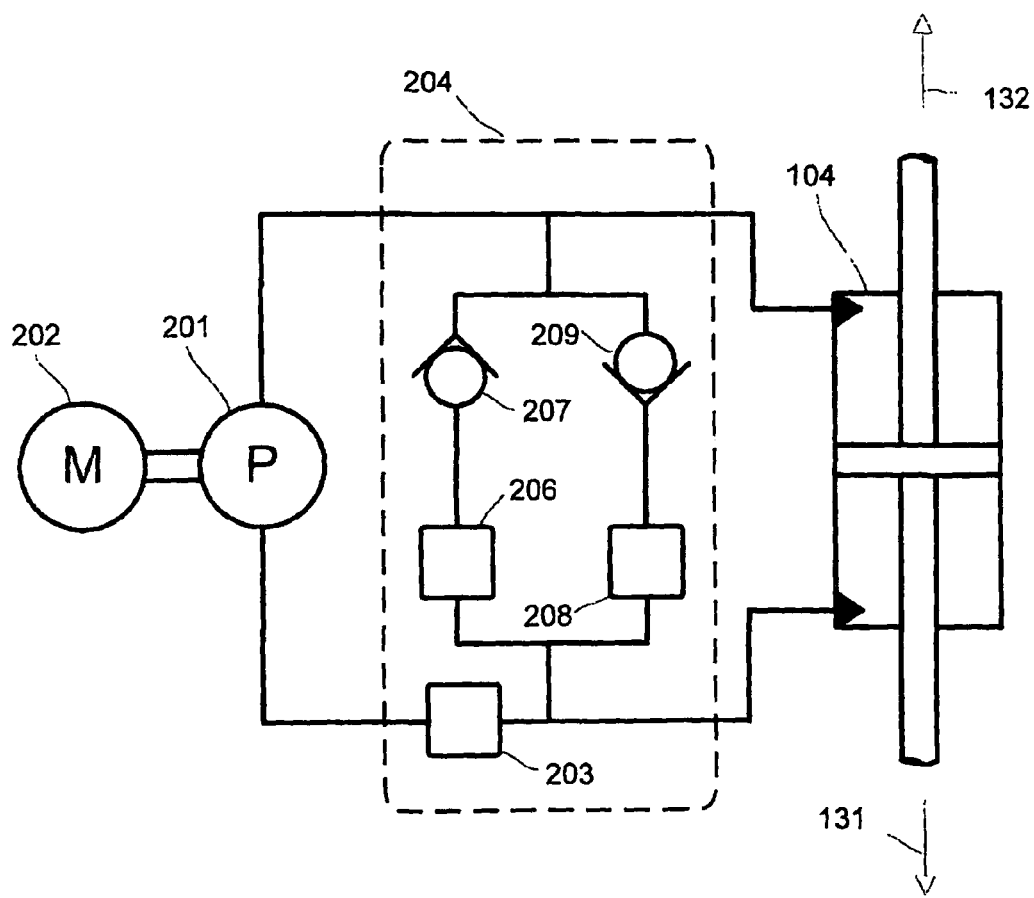
FIG. 5 is a diagram of the hydraulic valve circuit of FIG. 4, further comprising a second check valve.

In some embodiments, as shown in FIG. 5, hydraulic valve circuit 204, includes a second check valve 209 and second controllable valve 208 installed in series relative to each other and installed in parallel with serially installed first controllable valve 206 and first check valve 207. The operation of this embodiment is similar to the operation of the embodiment shown in FIG. 4 except it allows free flexion of torque generator 104 if second controllable valve 208 is open without compromising the ability to inject power in the flexion direction of torque generator 104. Similar to the embodiment of FIG. 4, when hydraulic valve circuit 204 of FIG. 5 operates in its actuated mode, first controllable valve 206 and second controllable valve 208 are closed and that allows one to control the motion of knee mechanism 107 or impose desirable torque onto knee mechanism 107.

Both first controllable valve 206 and second controllable valve 208 comprise any valve or combination of valves that allow for variation or adjustment of their openings either electronically or manually. Examples of first controllable valve 206 and second controllable valve 208 include, without limitation, a flow control valve, a pressure control valve, actuated needle valves, solenoid valves and an on-off valve.

Figure 6:
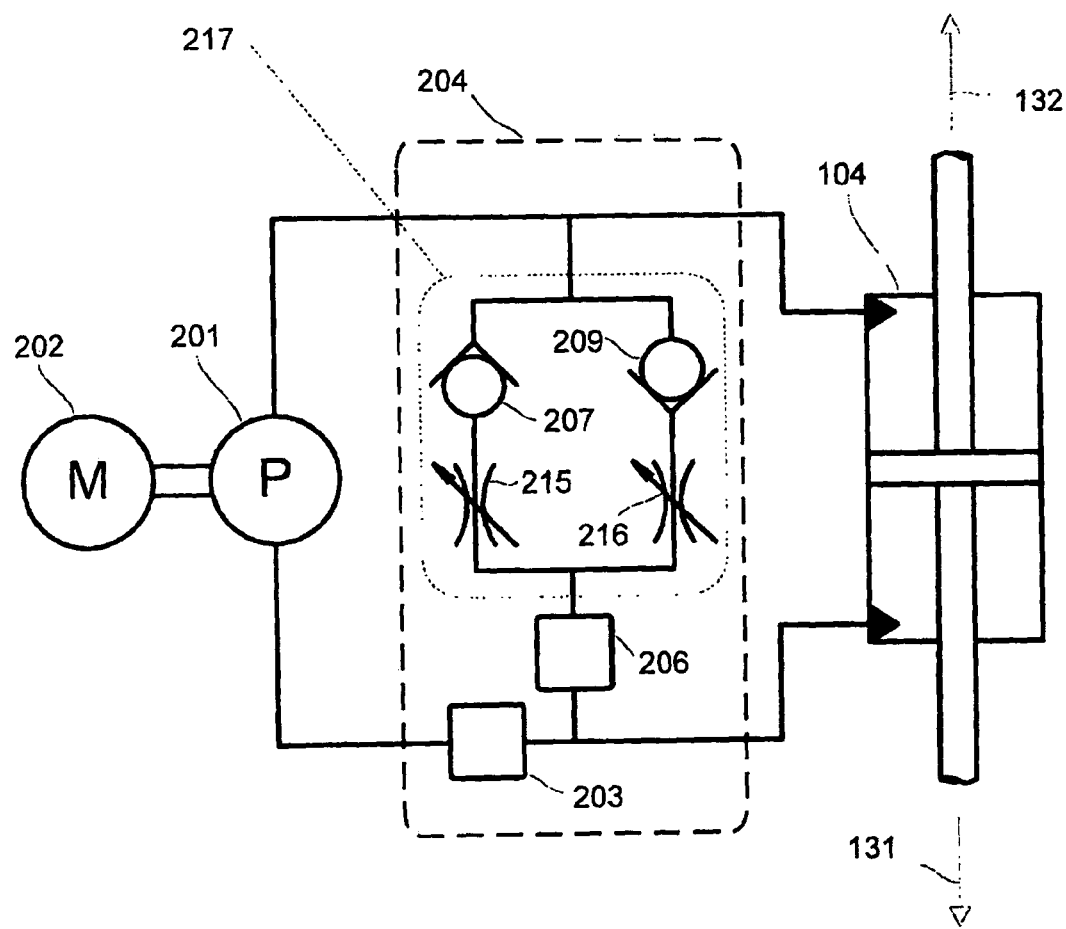
FIG. 6 is a diagram of an alternative hydraulic valve circuit including a parallel path circuit.

FIG. 6 shows another embodiment of hydraulic valve circuit 204. The embodiment of hydraulic valve circuit 204 of FIG. 6 is the same as embodiment of FIG. 3 except first check valve 207 in FIG. 3 is replaced by parallel path circuit 217. Parallel path circuit 217 comprises a first check valve 207 and a first adjustable restrictor valve 215 installed in series relative to each other and installed in parallel with serially installed second check valve 209 and a second adjustable restrictor valve 216.

In operation, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107. When semi-actuated prosthetic knee 100 operates in its un-actuated mode, pump valve 203 is closed so that no flow passes through hydraulic pump 201. Through the use of signal processor 130, one can adjust the opening of first controllable valve 206 to modulate the resistance of fluid flow in torque generator 104. Adjustable restrictor valve 215 is adjusted to provide resistance to fluid flow in the extension direction of torque generator 104. Adjustable restrictor valve 216 is adjusted to provide resistance to fluid flow in the flexion direction of torque generator 104. The ability to modulate the resistance of fluid flow in torque generator 104 allows one to control the resistance of knee mechanism 107 to forces and torques, with reduces use of electric power since electric motor 202 is not consuming any electric power in this un-actuated mode.

Figure 7:
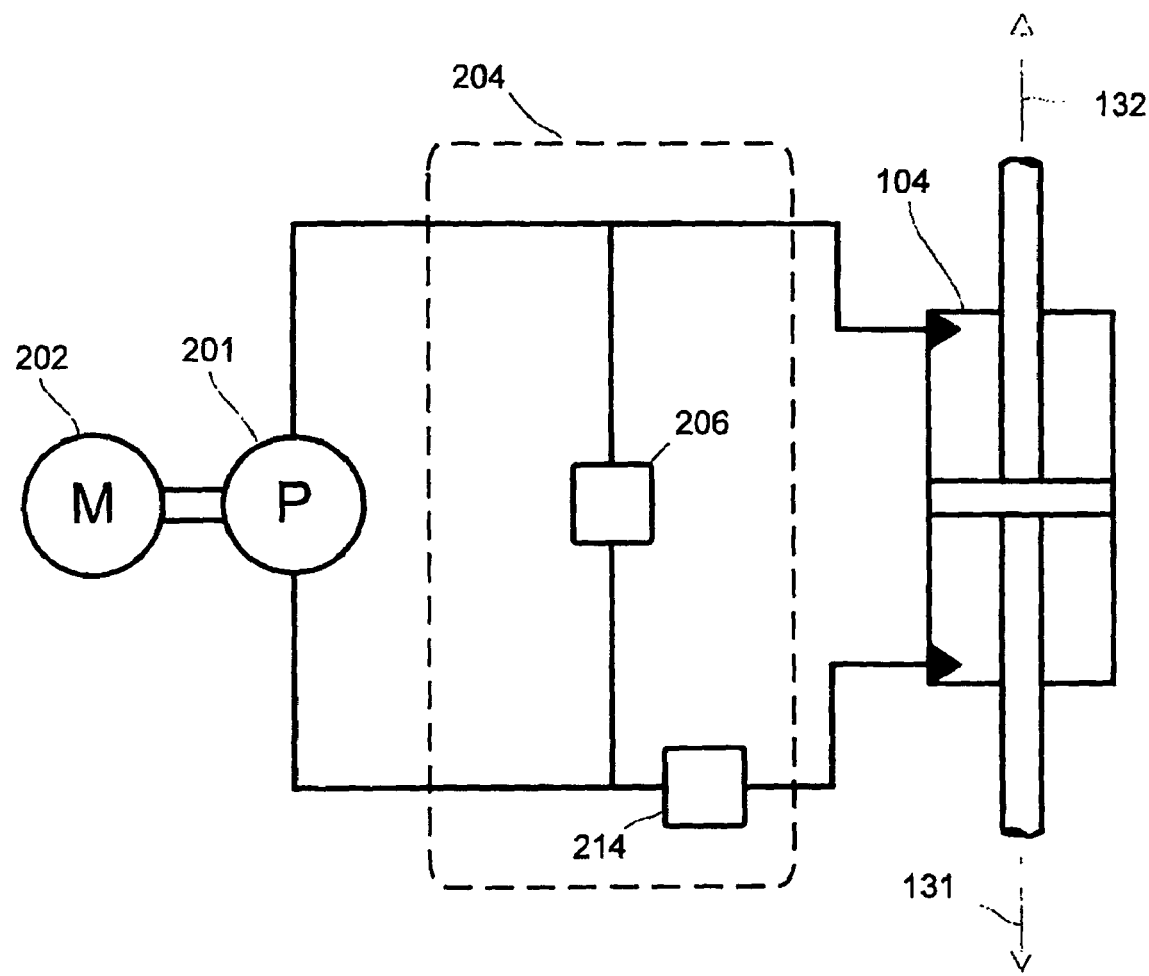
FIG. 7 is a diagram of an alternative hydraulic valve circuit including an actuator valve.

In some embodiments, as shown in FIG. 7, hydraulic valve circuit 204 comprises a first controllable valve 206 capable of controlling the hydraulic flow in two directions and an actuator valve 214 serially connected to each other. In this embodiment, torque generator 104 is coupled to two free ports of this serially connected first controllable valve 206 and said actuator valve 214. Hydraulic pump 201 is coupled to two ports of first controllable valve 206.

In operation, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107. When semi-actuated prosthetic knee 100 operates in its un-actuated mode, through the use of signal processor 130, one can adjust the opening of actuator valve 214 to modulate the resistance of fluid flow in torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode.

When semi-actuated prosthetic knee 100 operates in a power regenerative mode, actuator valve 214 is not closed, allowing at least a portion of the hydraulic flow from torque generator 104 to turn hydraulic pump 201 while motor controller 128 applies a non-zero current onto electric motor 202 to resist the hydraulic flow in hydraulic pump 201.

Figure 8:
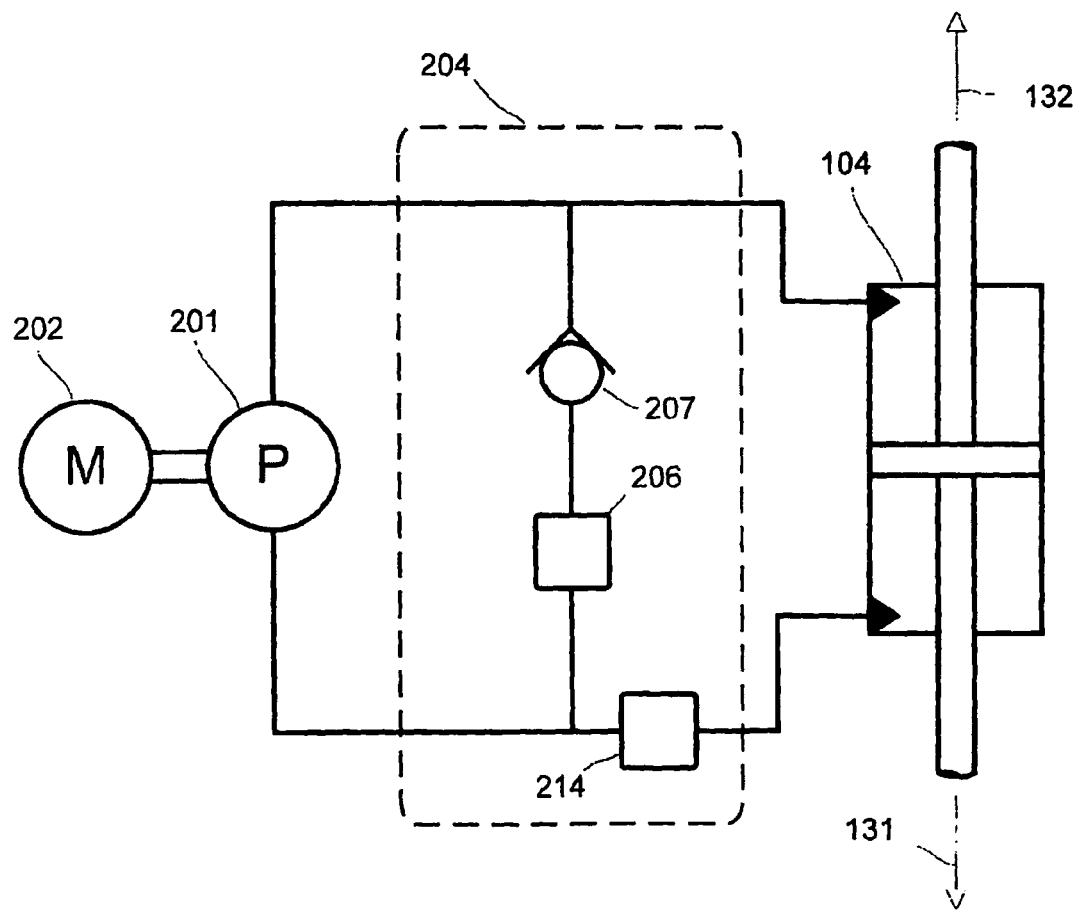
FIG. 8 is a diagram of the hydraulic valve circuit of FIG. 7, further comprising a first check valve.

In some embodiments, as shown in FIG. 8, hydraulic valve circuit 204, among other components, further comprises a first check valve 207 installed in series with first controllable valve 206 allowing the hydraulic flow in one direction only. In comparison with the embodiment of FIG. 7, this embodiment constrains the resistance of fluid flow in torque generator 104 in the flexion direction to always be more than the flow resistance that hydraulic pump 201 creates. It further allows free extension of torque generator 104 if first controllable valve 206 is open without compromising the ability to inject power in the extension direction of torque generator 104. When semi-actuated prosthetic knee 100 operates in its actuated mode, first controllable valve 206 is closed. This allows one to control the motion of knee mechanism 107 or impose desirable torque onto knee mechanism 107.

Figure 9:
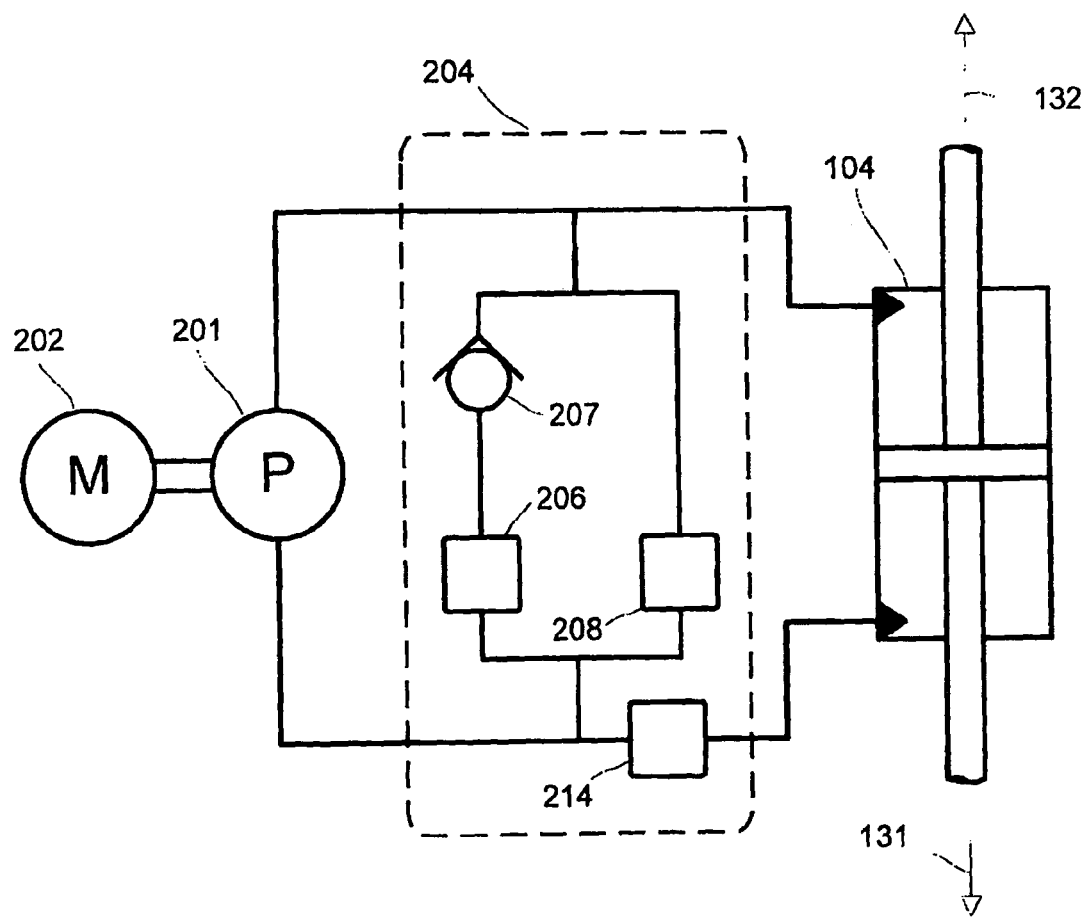
FIG. 9 is a diagram of the hydraulic valve circuit of FIG. 8, further comprising a second controllable valve.

In some embodiments, as shown in FIG. 9, hydraulic valve circuit 204, among other components, further comprises a second controllable valve 208 installed in parallel with serially-installed first controllable valve 206 and first check valve 207. The operation of this embodiment is similar to the operation of the embodiment shown in FIG. 8 except this embodiment does not constrain the resistance of fluid flow in torque generator 104 in the flexion direction to always be more than the flow resistance that hydraulic pump 201 creates. In operation, when hydraulic valve circuit 204 of FIG. 9 operates in its actuated mode, first and second controllable valves 206 and 208 are closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107.

Figure 10:
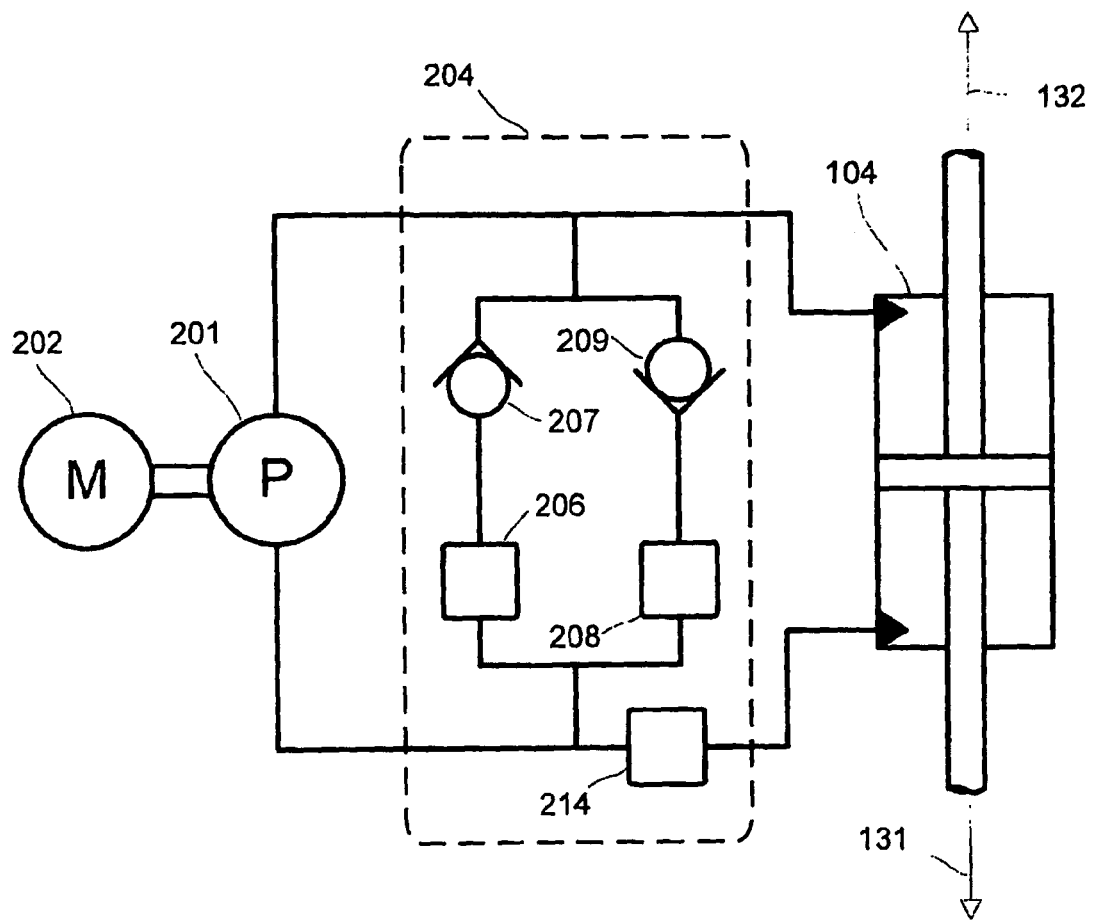
FIG. 10 is a diagram of the hydraulic valve circuit of FIG. 9, further comprising a second check valve.

In some embodiments, as shown in FIG. 10, hydraulic valve circuit 204 comprises a second check valve 209 and second controllable valve 208 installed in series relative to each other and installed in parallel with serially installed first controllable valve 206 and first check valve 207. The operation of this embodiment is similar to the operation of the embodiment shown in FIG. 9 except it allows free flexion of torque generator 104 if second controllable valve 208 is open without compromising the ability to inject power in the flexion direction of torque generator 104. When semi-actuated prosthetic knee 100 operates in its actuated mode, first and second controllable valves 206 and 208 are closed. This allows one to control the motion of knee mechanism 107 or impose desirable torque onto knee mechanism 107.

Figure 11:
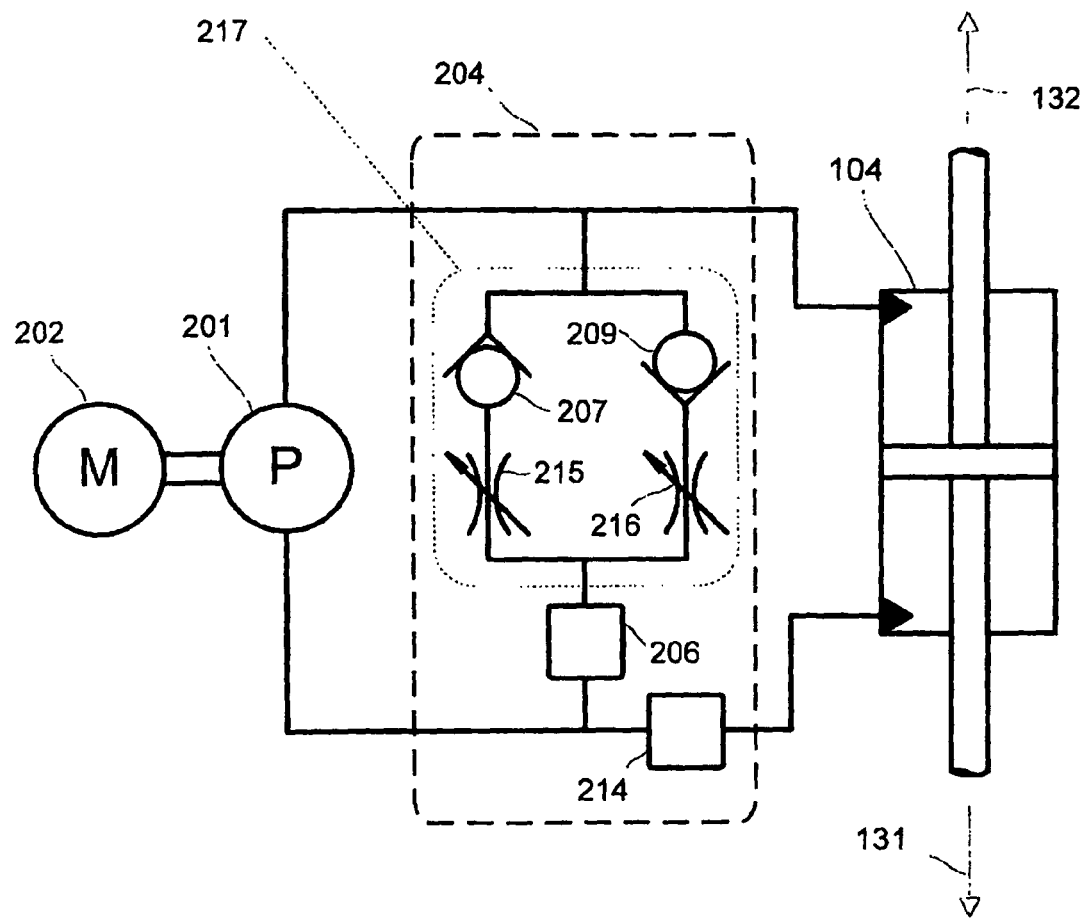
FIG. 11 is a diagram of an alternative hydraulic valve circuit including a parallel path circuit.

FIG. 11 shows another embodiment of hydraulic valve circuit 204. The embodiment of hydraulic valve circuit 204 of FIG. 11 is the same as embodiment of FIG. 8 except check valve 207 in FIG. 8 is replaced by parallel path circuit 217. Parallel path circuit 217 comprises a first check valve 207 and first adjustable restrictor valve 215 installed in series relative to each other and installed in parallel with serially installed second check valve 209 and second adjustable restrictor valve 216.

In operation, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107. When semi-actuated prosthetic knee 100 operates in its un-actuated mode, one can adjust the opening of actuator valve 214 to modulate the resistance of fluid flow in torque generator 104. First adjustable restrictor valve 215 is adjusted to provide resistance to fluid flow in the extension direction of torque generator 104. Second adjustable restrictor valve 216 is adjusted to provide resistance to fluid flow in the flexion direction of torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode.

Figure 12:
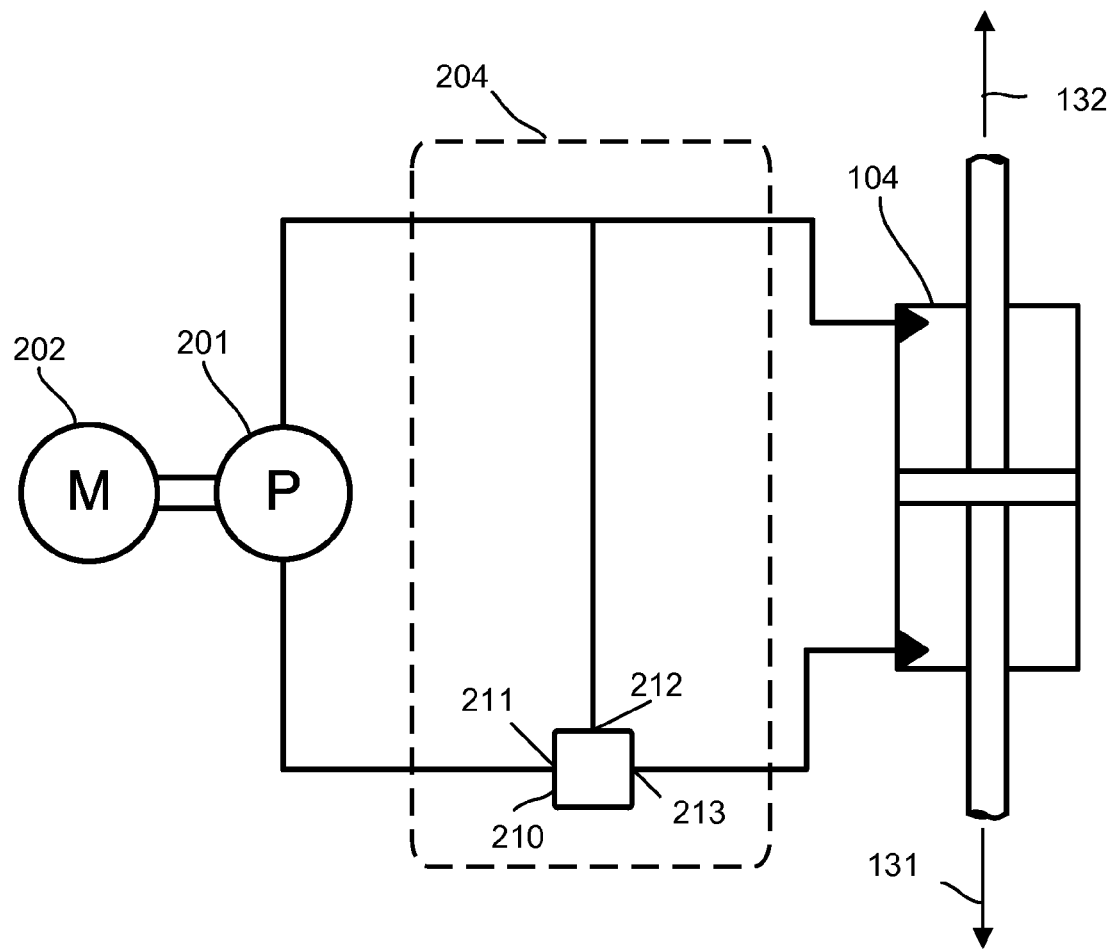
FIG. 12 is a diagram of an alternative hydraulic valve circuit including a three-way valve.

In some embodiments, as shown in FIG. 12, hydraulic valve circuit 204 comprises a three-way valve 210 capable of controlling the hydraulic flow. In operation, when semi-actuated prosthetic knee 100 operates in its actuated mode, three-way valve connects port 211 to port 213 and blocks port 212. This allows for fluid flow between hydraulic pump 201 and torque generator 104 such that the entire hydraulic pump output flow travels to torque generator 104. This further allows signal processor 130 to control torque generator 104 by controlling electric motor 202. The ability to inject power to torque generator 104, in this actuated mode, allows one to control the motion of knee mechanism 107 or impose desirable torque onto knee mechanism 107. When semi-actuated prosthetic knee 100 operates in an un-actuated mode, three-way valve 210 connects port 212 to port 213. Through the use of signal processor 130, one can adjust the opening of port 213 to modulate the resistance of fluid flow in torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode. When semi-actuated prosthetic knee 100 operates in a power regenerative mode, three-way valve 210 connects port 211 to port 213 allowing at least a portion of the hydraulic flow from torque generator 104 to turn hydraulic pump 201 while motor controller 128 applies a non-zero current onto electric motor 202 to resist the hydraulic flow in hydraulic pump 201.

Figure 13:
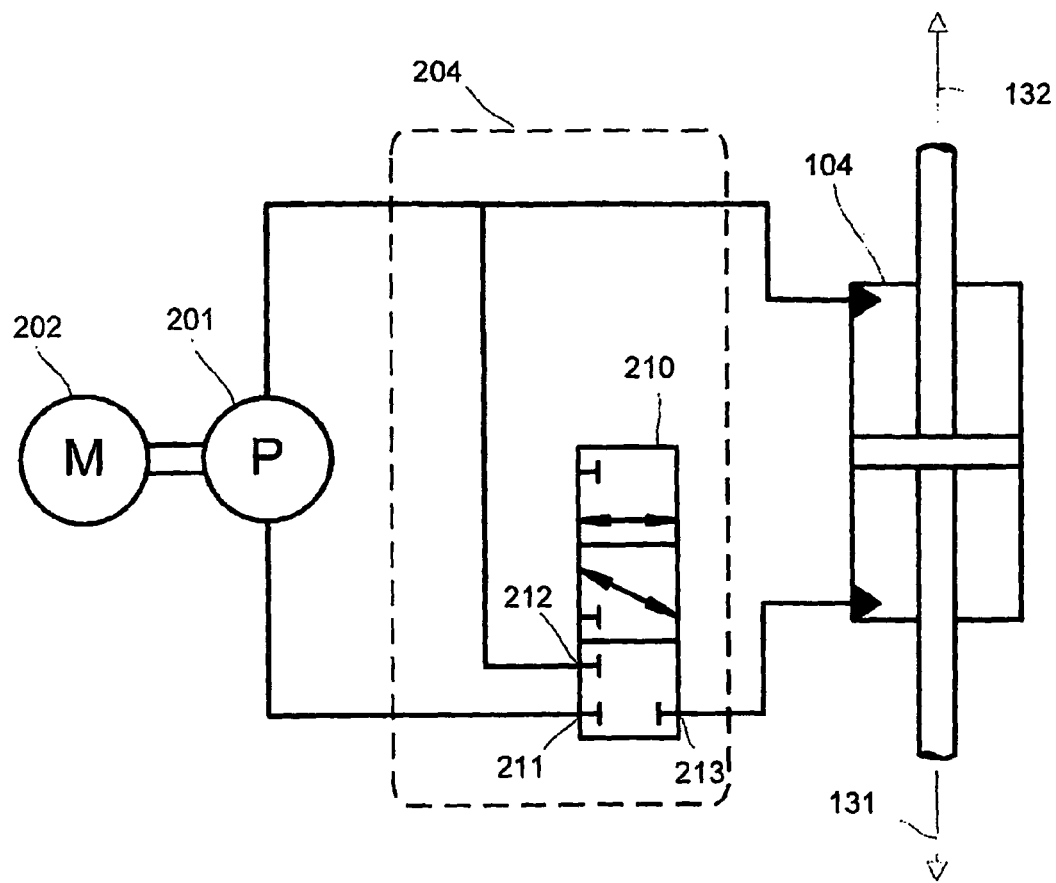
FIG. 13 depicts the three way valve of the hydraulic valve circuit of FIG. 12 in use.

FIG. 13 shows a realization of the embodiment of FIG. 12. More specifically, FIG. 13 shows a three-way valve 210 that has at least three positions. When three-way valve 210 is in its first position, three-way valve connects port 211 to port 213 and blocks port 212. This allows semi-actuated prosthetic knee 100 to operate in actuated mode. When three-way valve 210 is in its second position, it connects port 212 to port 213 and blocks port 211. Through the use of signal processor 130, one can adjust the opening of port 212, port 213 or both port 212 and 213 to modulate and adjust properly the resistance of fluid flow in torque generator 104. When three-way valve 210 is in its third position (shown in FIG. 13), none of the ports are connected to each other.

Figure 14:
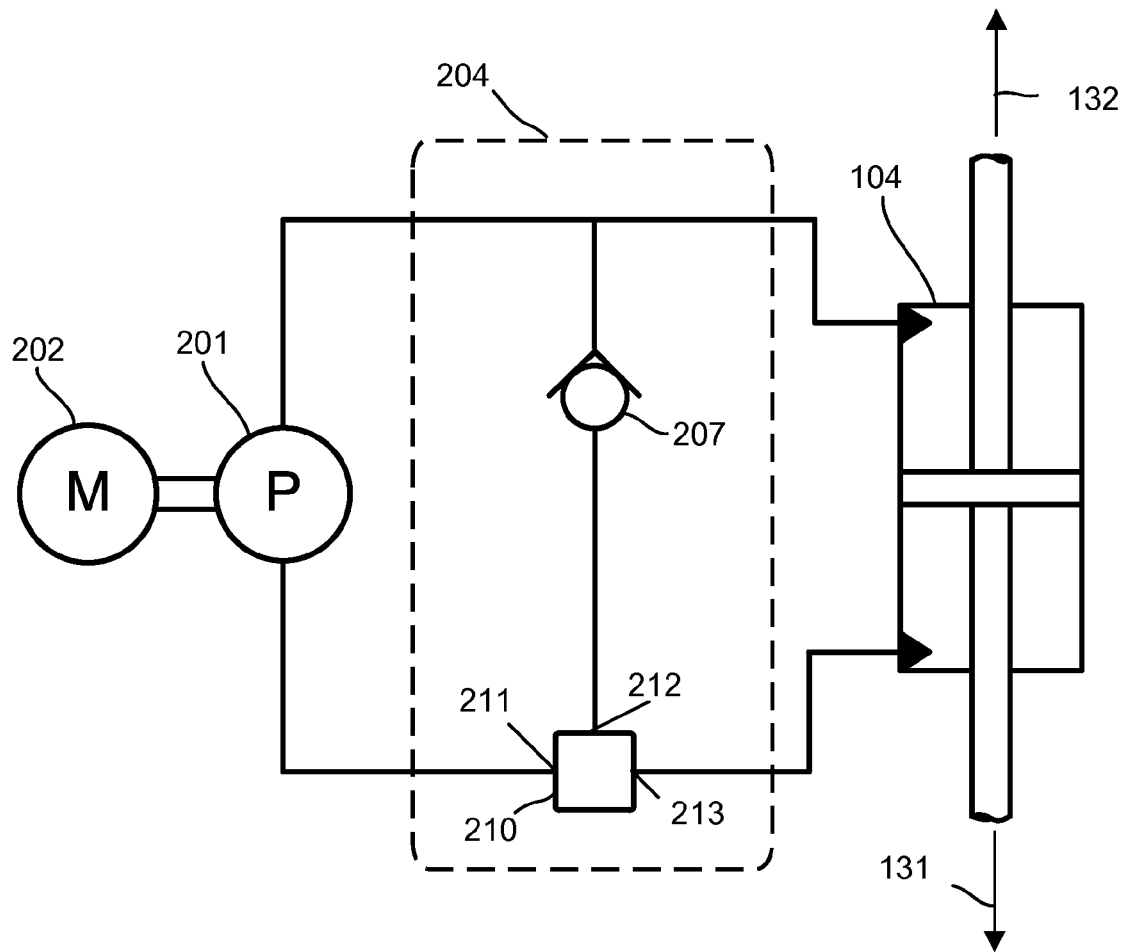
FIG. 14 is a diagram of the hydraulic valve circuit of FIG. 12, further comprising a first check valve.

FIG. 14 shows another embodiment of the embodiment of FIG. 12 where hydraulic valve circuit 204 further comprises a first check valve 207 coupled to port 212. In comparison with the embodiment of FIG. 12, this embodiment constrains the range of resistance of fluid flow in torque generator 104 in flexion direction to always be more than the flow resistance that hydraulic pump 201 creates. It further allows free extension of torque generator 104 if all ports 211, 212 are 213 are connected to each other without compromising the ability to inject power in the extension direction of torque generator 104. When semi-actuated prosthetic knee 100 operates in its actuated mode, three-way valve 210 connects port 211 to port 213 and blocks port 212. This allows for fluid flow between hydraulic pump 201 and torque generator 104 such that the entire hydraulic pump output flow travels to torque generator 104. This further allows signal processor 130 to control the motion of knee mechanism 107 or impose desirable torque onto knee mechanism 107 by controlling electric motor 202.

Figure 15:
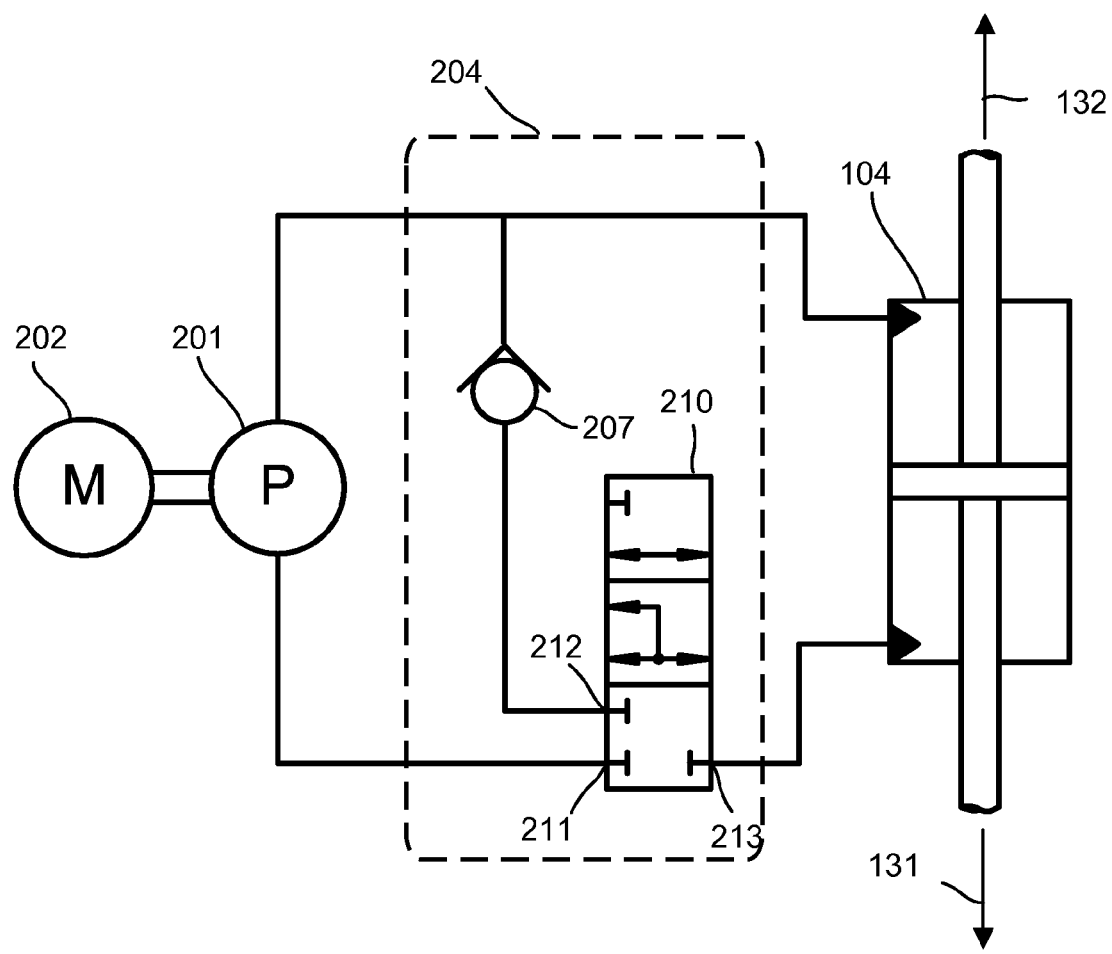
FIG. 15 depicts the three way valve of the hydraulic valve circuit of FIG. 14 in use.

FIG. 15 shows a realization of the embodiment of FIG. 14. FIG. 15 shows a three valve 210 that has at least three positions. When three-way valve 210 is in its first position (actuated mode), three-way valve 210 connects port 211 to port 213 and blocks port 212. When three-way valve 210 is in its second position, all ports are connected to each other. Through the use of signal processor 130, one can adjust the opening of port 212, port 213 or both port 212 and 213 to properly modulate and adjust the resistance of fluid flow in torque generator 104. When three-way valve 210 is in its third position (shown in FIG. 15), none of the ports are connected to each other.

FIG. 16 shows the same embodiment of FIG. 15 with a few added features. A reservoir 230 ensures sufficient oil is in the system in the presence of any leakage or thermal expansion. Two check valves 228 and 229 ensure hydraulic fluid is not pushed back to reservoir 230. Two hydraulic fluid paths 231 and 232 ensure any leakage from the three-way valve 210 and hydraulic pump 201 are fed back to reservoir 230. Pressure sensors 126 and 127 measure the hydraulic fluid pressure in first and second chambers of torque generator 104. A filter 233 collects any contaminants in the fluid.

Figure 17:
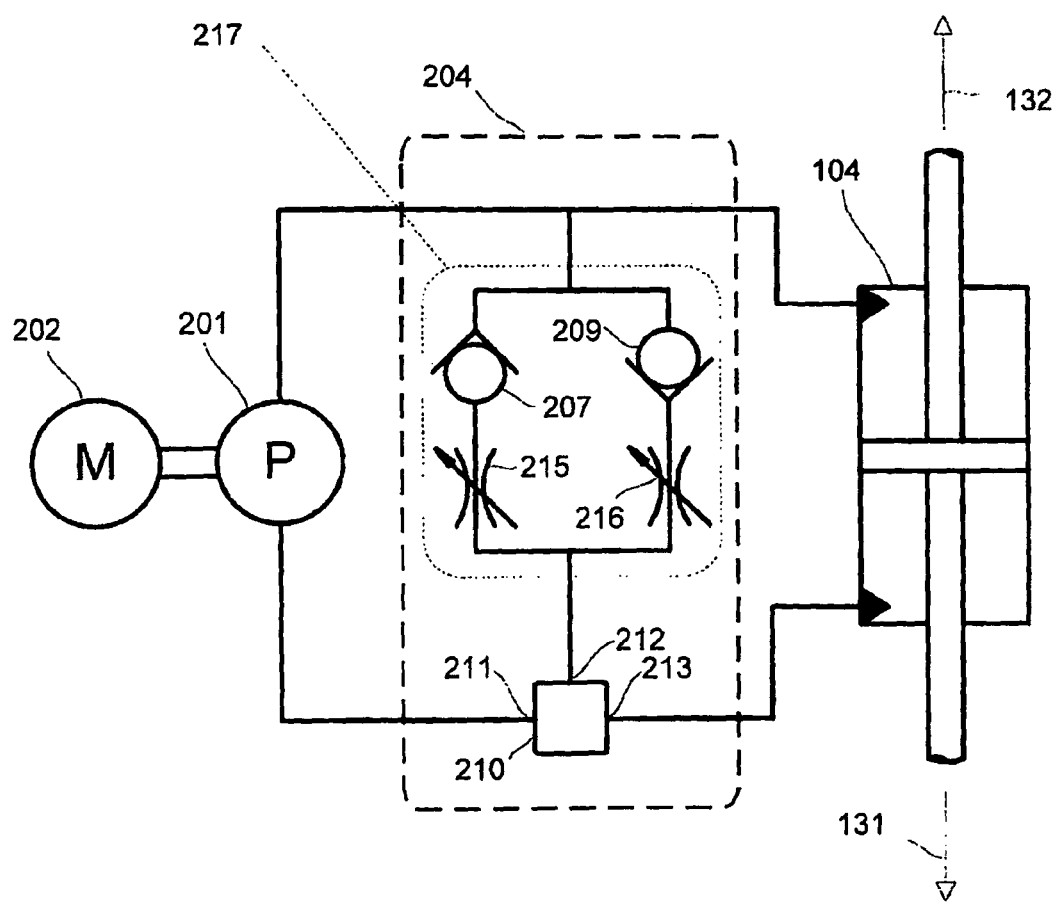
FIG. 17 is a diagram of the hydraulic valve circuit of FIG. 12, further including a parallel path circuit.

FIG. 17 shows another embodiment of FIG. 12 wherein hydraulic valve circuit 204 further comprises a parallel path circuit 217 coupled to port 212. In operation, when semi-actuated prosthetic knee 100 operates in its actuated mode, three-way valve 210 connects port 211 to port 213 and blocks port 212. This allows for fluid flow between hydraulic pump 201 and torque generator 104 such that the entire said hydraulic pump output flow travels to torque generator 104. This further allows signal processor 130 to control torque generator 104 by controlling electric motor 202. The ability to inject power to torque generator 104 in this actuated mode allows one to control the motion of knee mechanism 107 or impose desirable torque onto knee mechanism 107. When semi-actuated prosthetic knee 100 operates in its un-actuated mode, three-way valve 210 connects port 212 to port 213 and blocks port 211. Through the use of signal processor 130, one can adjust the opening of port 213 or port 212 to modulate the resistance of fluid flow in torque generator 104. First adjustable restrictor valve 215 is adjusted to provide resistance to fluid flow in the extension direction of torque generator 104. Second adjustable restrictor valve 216 is adjusted to provide resistance to fluid flow in the flexion direction of torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode.

Figure 18:
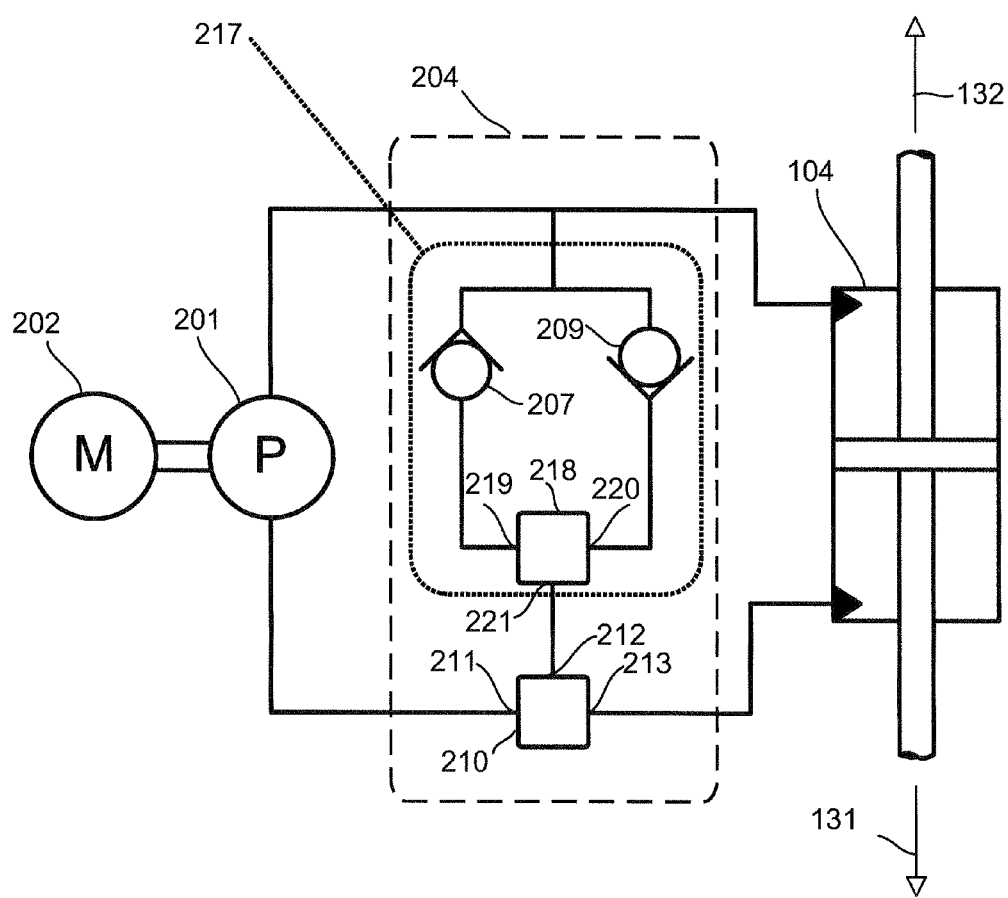
FIG. 18 is a diagram of an alternative hydraulic valve circuit including a second three-way valve.

FIG. 18 shows another embodiment of hydraulic valve circuit 204. The embodiment of FIG. 18 is the same as the embodiment of FIG. 17 except adjustable restrictor valves 215 and 216 are replaced by a second three-way valve 218. In operation when semi-actuated prosthetic knee 100 operates in an actuated mode, three-way valve 210 connects port 211 to port 213 and blocks port 212. This allows for fluid flow between hydraulic pump 201 and torque generator 104 such that the entire hydraulic pump output flow travels to torque generator 104. This further allows signal processor 130 to control torque generator 104 by controlling electric motor 202. When semi-actuated prosthetic knee 100 operates in an un-actuated mode, first three-way valve 210 connects port 212 to port 213. Second three-way valve 218 modulates the resistance to hydraulic flow between a port 219 and a port 221 when torque generator 104 moves in the extension direction and modulates the resistance to hydraulic flow between a port 220 and port 221 when torque generator 104 moves in the flexion direction. This embodiment allows free extension of torque generator 104 without compromising the ability to inject power in the extension direction of torque generator 104 if port 219 and port 221 are connected and port 220 is blocked and if ports 211, 212 and 213 are connected to each other. This embodiment further allows free flexion of torque generator 104 without compromising the ability to inject power in the flexion direction of torque generator 104 if port 220 and port 221 are connected and port 219 is blocked and if ports 211, 212 and 213 are connected to each other.

Figure 19:
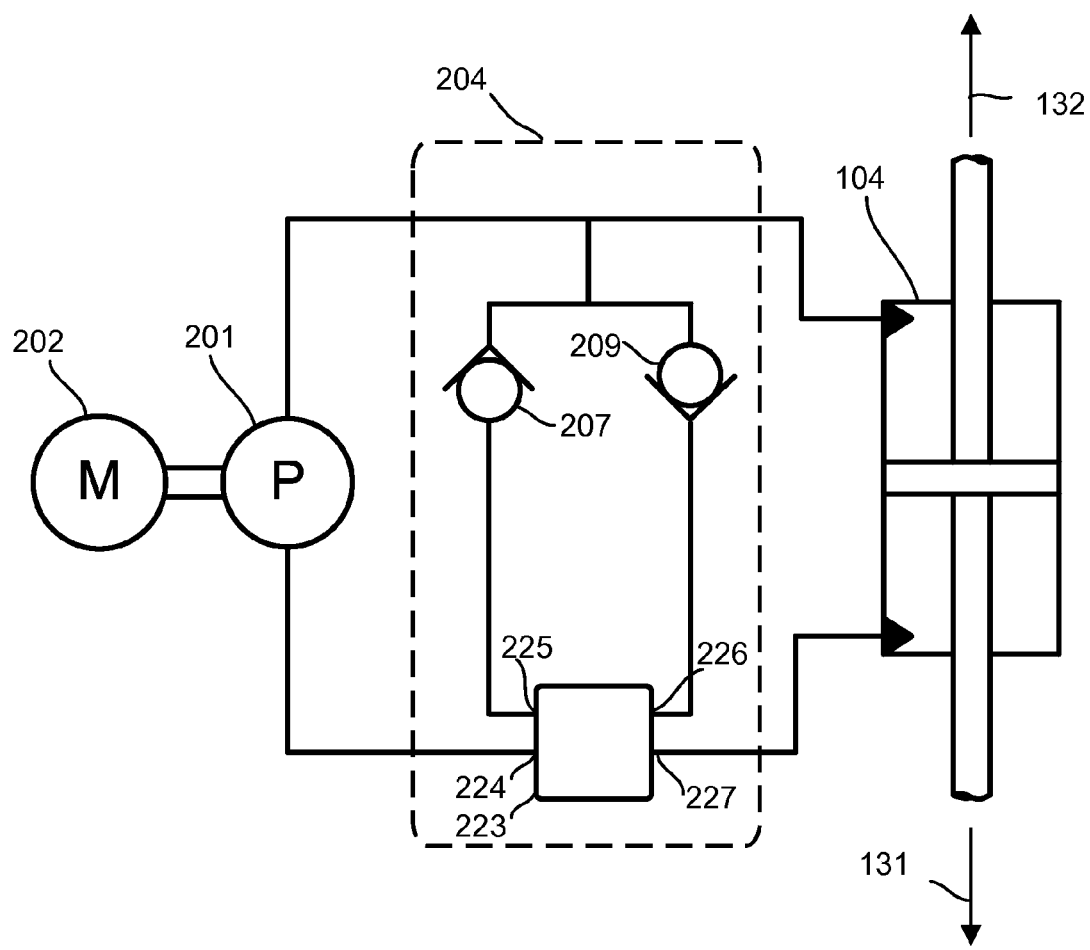
FIG. 19 is a diagram of an alternative hydraulic valve circuit including a four-way valve.

FIG. 19 shows another embodiment of hydraulic valve circuit 204. The embodiment of FIG. 19 is the same as the embodiment of FIG. 18 except two three-way valves 210 and 218 are replaced by a four way valve 223. In operation when semi-actuated prosthetic knee 100 operates in an actuated mode, four-way valve 223 connects a port 224 to a port 227 and blocks ports 225 and 226. This allows for fluid flow between hydraulic pump 201 and torque generator 104 such that the entire said hydraulic pump output flow travels to torque generator 104. This further allows signal processor 130 to control torque generator 104 by controlling electric motor 202. When semi-actuated prosthetic knee 100 operates in an un-actuated mode, four-way valve 223 modulates the resistance to hydraulic flow between port 225 and port 227 when torque generator 104 moves in the extension direction and modulates the resistance to hydraulic flow between port 226 and port 227 when torque generator 104 moves in the flexion direction. This embodiment allows free extension of torque generator 104 without compromising the ability to inject power in the extension direction of torque generator 104 if ports 224, 225, and 227 are connected and port 226 is blocked. This embodiment further allows free flexion of torque generator 104 without compromising the ability to inject power in the flexion direction of torque generator 104 if ports 224, 226, and 227 are connected and port 225 is blocked.

As can be seen from FIGS. 1 through 19, hydraulic power unit 200 comprises two paths that connect to torque generator 104: one through hydraulic pump 201 and the second through a hydraulic valve circuit 204. In the actuated mode, hydraulic pump 201 hydraulically couples to torque generator 104. In un-actuated mode, the flow to torque generator 104 is modulated by at least one valve.

Figure 20:
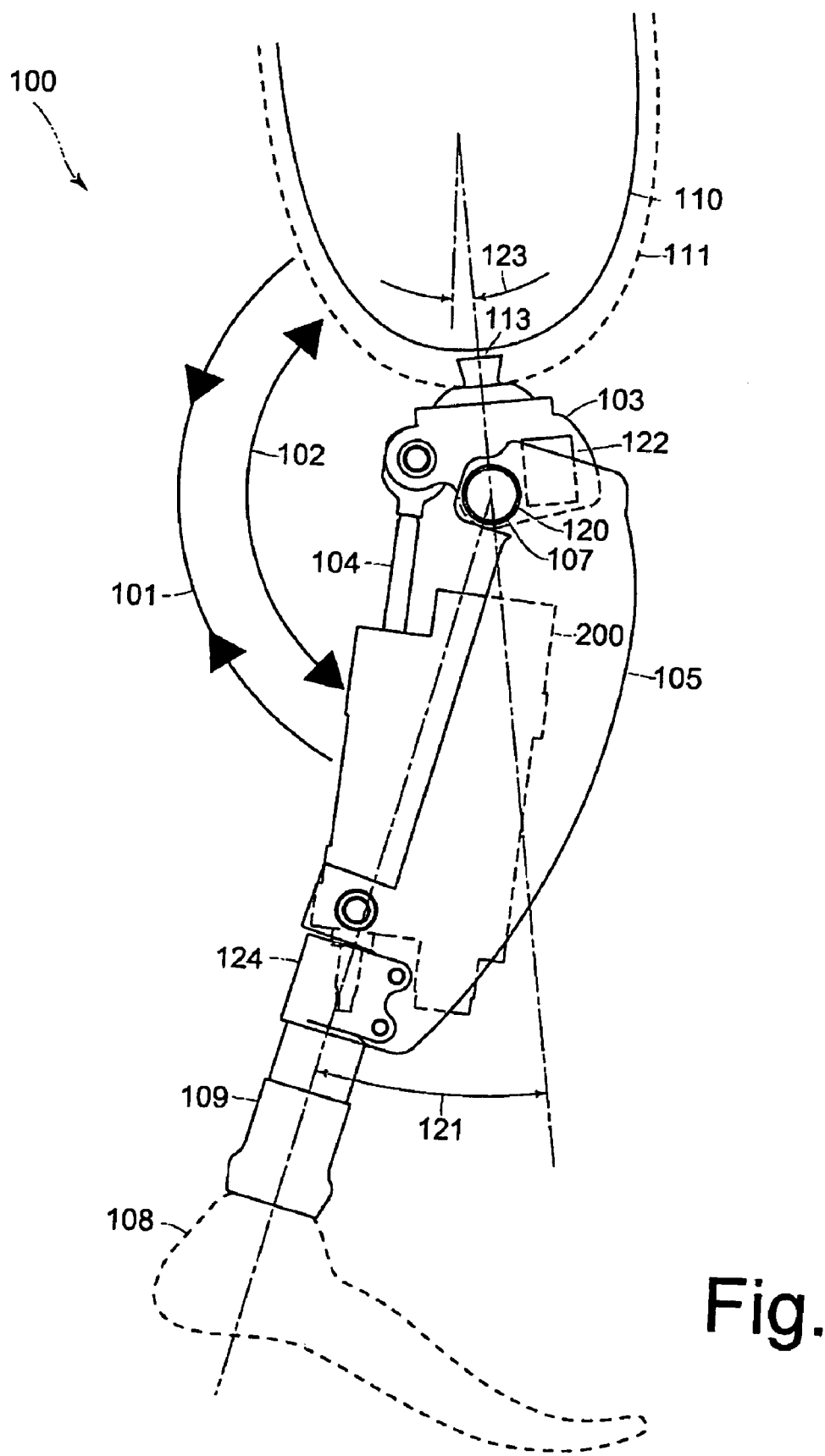
FIG. 20 is a side view of the semi-actuated prosthetic knee of FIG. 1.

FIG. 20 represents the schematic of one embodiment of semi-actuated prosthetic knee 100. As previously noted, semi-actuated prosthetic knee 100, among other components, comprises a thigh link 103, a shank link 105, and a knee mechanism 107, coupled by torque generator 104. Knee mechanism 107 is configured to allow movement of thigh link 103 relative to shank link 105 along flexion direction 101 and extension direction 102. Semi-actuated prosthetic knee 100 is configurable to be coupled to an above-knee amputee's remaining lower limb 110 through a socket 111. More specifically, socket 111 is coupled to thigh link 103 with a pyramid adapter 113 or similar adapter known in the art. An ankle pylon 109 connects shank link 105 to artificial foot 108 through stance sensor 124. Knee angle sensor 120 measures an angle 121 between thigh link 103 and shank link 105. Thigh angle sensor 122 located on thigh link 103 measures an absolute angle 123 of thigh link 103. The profile of hydraulic power unit 200 is shown in FIG. 20.

Figure 21:
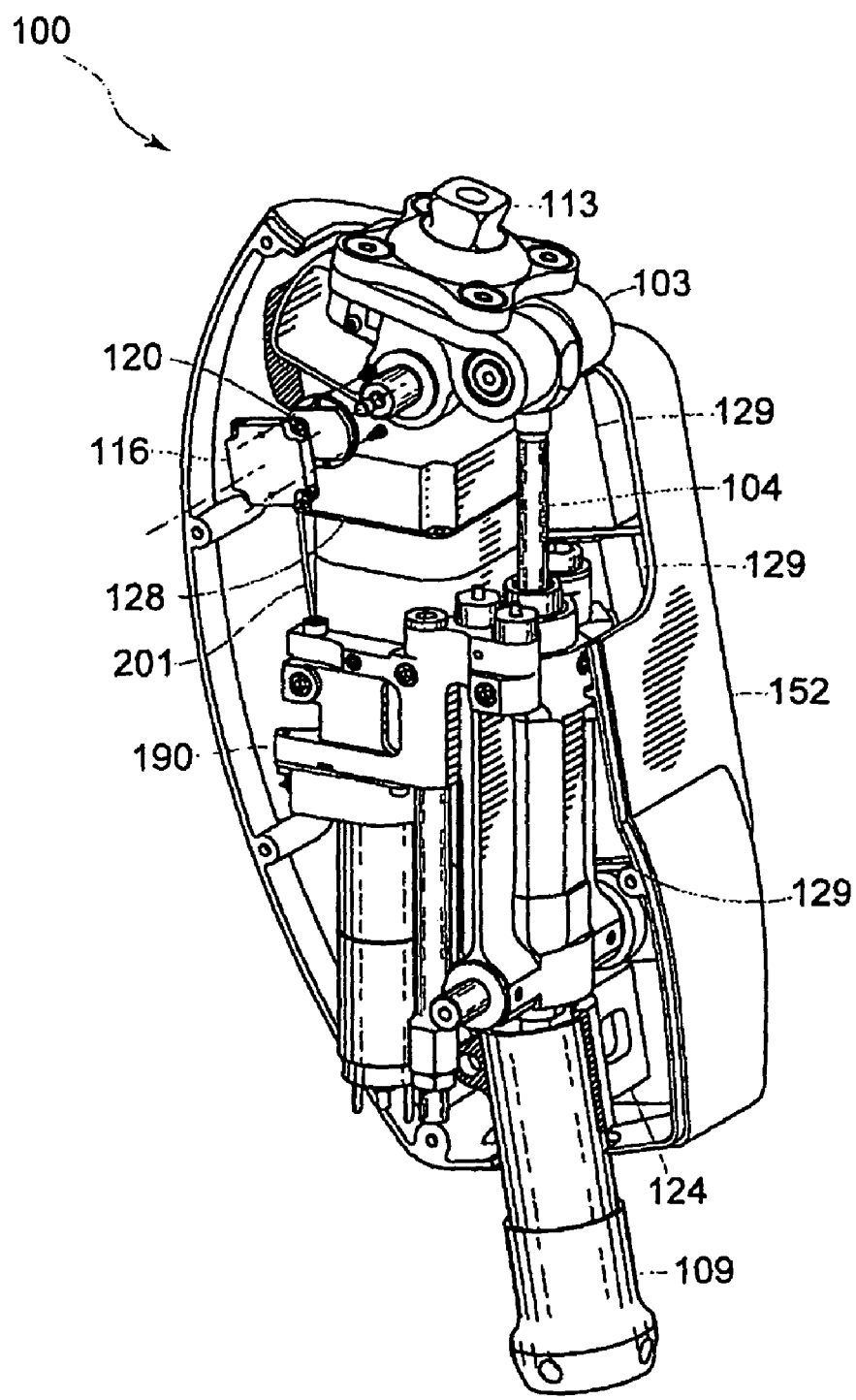
FIG. 21 is a more detailed perspective view of the semi-actuated prosthetic knee of FIG. 20.

FIGS. 21 and 22 represent a cutaway perspective drawing and exploded view of the semi-actuated prosthetic knee 100 presented in FIG. 20. In the embodiment of FIGS. 21 and 22, pyramid adapter 113 connects to thigh link 103. Thigh angle sensor 122 fixed to thigh link 103 comprises an accelerometer 133 and a gyroscope 134. A shaft 118 extending from thigh link 103 is stationary with respect to thigh link 103. Knee angle sensor 120 is in the form of a magnetic encoder fixed to an encoder housing 116 and stationary with respect to shank link 105. Magnetic encoder 120 measures the angle of a magnet 119 embedded in shaft 118. Shaft 118 is secured to thigh link 103 and turns inside needle bearings 135. Thrust bushings 136 provide axial support between thigh link 103 and knee mechanism 107. A bearing cover 115 protects needle bearing 135. Hydraulic power unit 200 comprises, among other elements, motor controller 128, hydraulic pump 201, a hydraulic manifold 190, torque generator 104 and pressure sensors 126 and 127. Power unit 200 pivots with respect to shank link 105 on needle bearings 137. Thrust bushings 138 provide axial support between power unit 200 and shank link 105. Torque generator 104 couples to thigh link 103 through needle bearings 139 to complete the linkage between thigh link 103, shank link 105, and torque generator 104. Stance sensor 124 connects shank link 105 to ankle pylon 109. Batteries 129 are used to provide electric power for the prosthetic knee 100.

Figure 23:
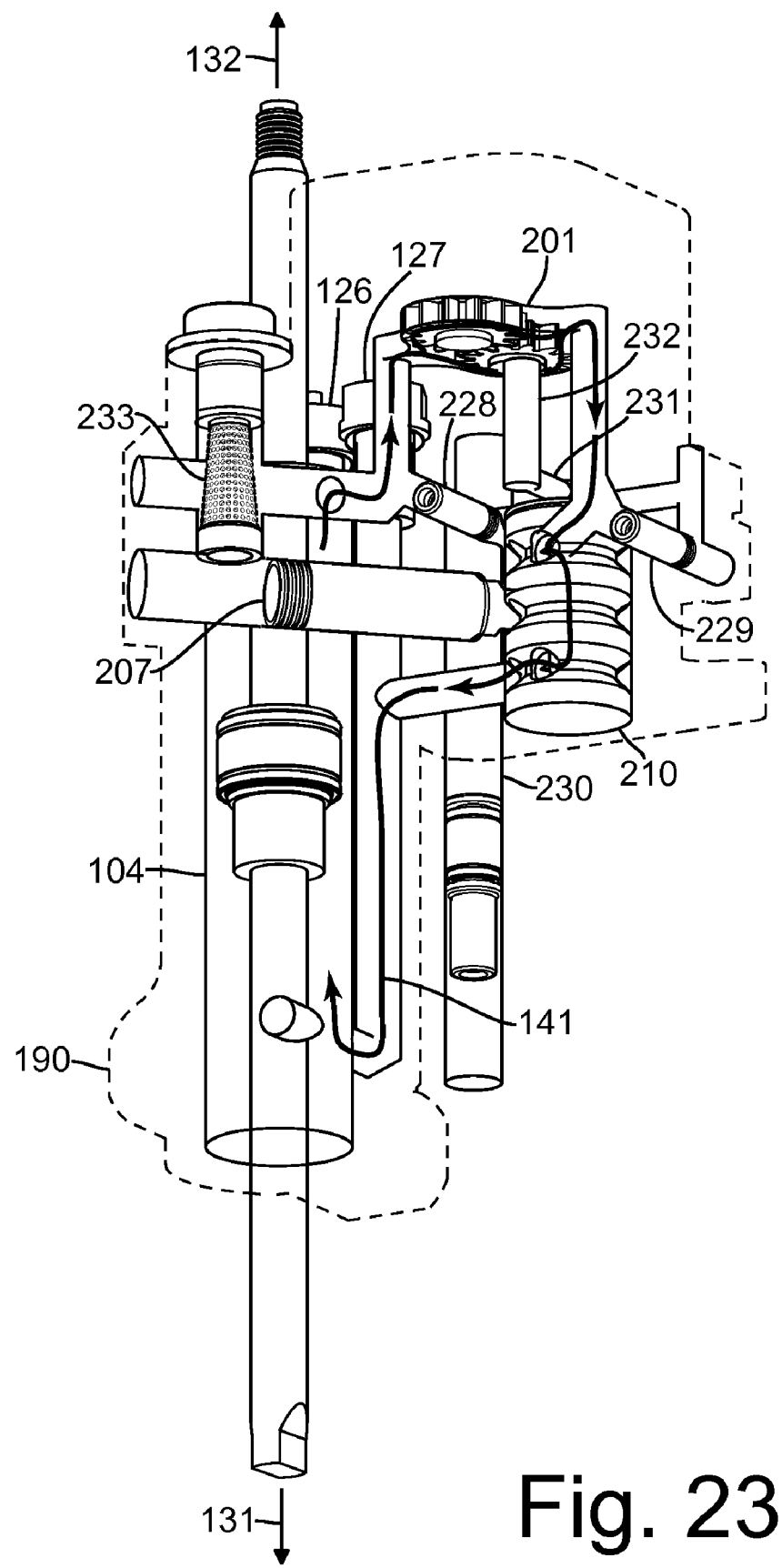
FIG. 23 is a partial perspective view of the hydraulic valve circuit of FIG. 16 with fluid flow during an actuated mode in extension.
Figure 24:
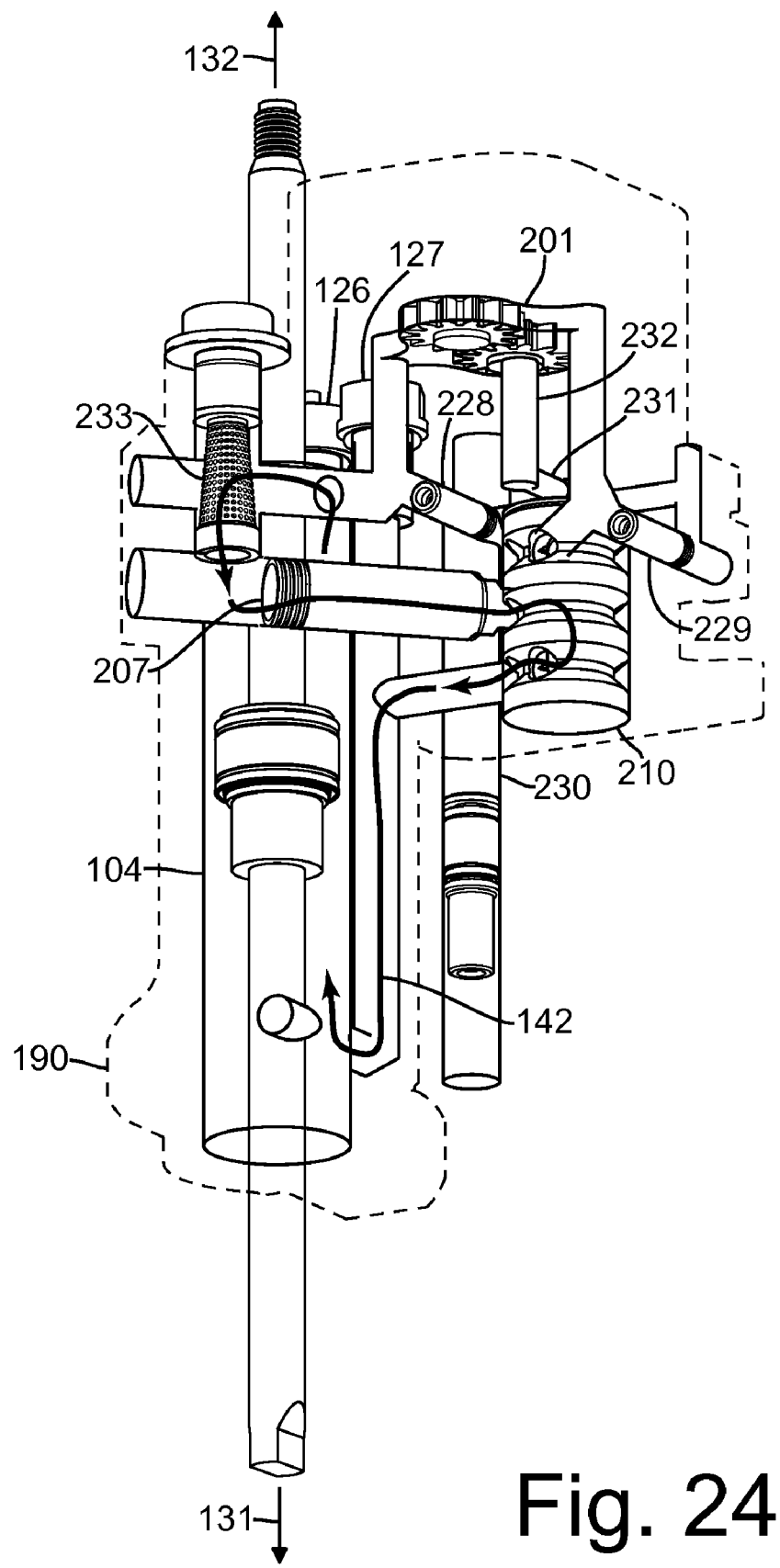
FIG. 24 is a partial perspective view of the hydraulic valve circuit of FIG. 16 with fluid flow during an un-actuated mode in extension.

FIG. 23 shows a perspective drawing of the hydraulic valve circuit shown in FIG. 16. An arrow 141 represents the path of hydraulic flow during an actuated mode in extension direction represented by arrow 132. Three-way valve 210 incorporates three ports 211, 212, and 213 (depicted in FIG. 16) that connect to hydraulic pump 201, check valve 207 and torque generator 104, respectively. Check valves 228 and 229 prevent the fluid flow back to reservoir 230. Hydraulic fluid paths 231 and 232 define passages from hydraulic pump 201 and three-way hydraulic valve 210 to reservoir 230. FIG. 24 also shows a perspective drawing of the hydraulic valve circuit of FIG. 16, where an arrow 142 shows the path of the hydraulic flow during un-actuated mode in extension direction.

Figure 25:
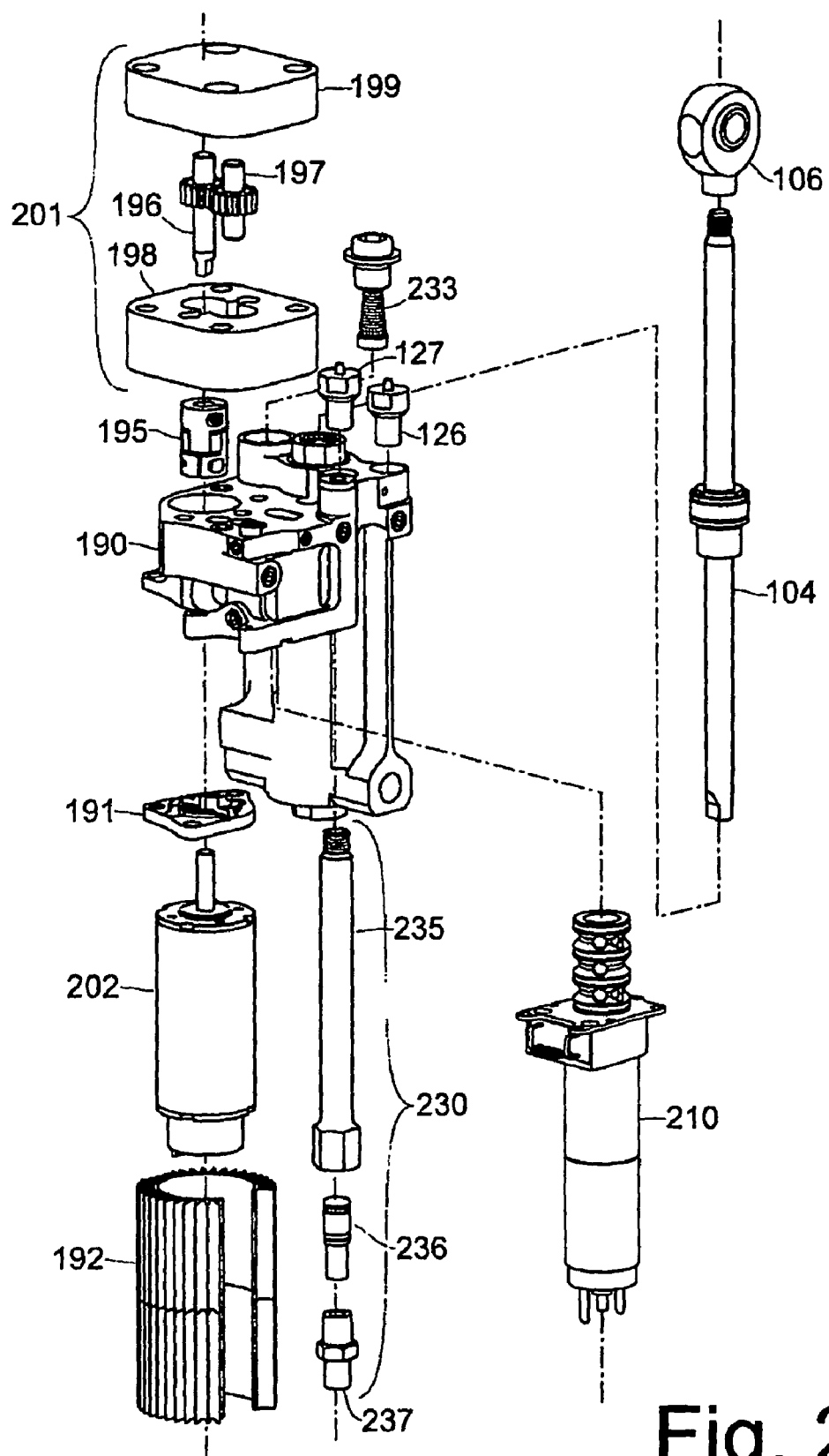
FIG. 25 is an exploded view of the power unit in FIG. 1.

FIG. 25 shows the exploded view of hydraulic power unit 200. Hydraulic pump 201 includes a pump cover 199 and a pump base 198. A driver gear 196 is coupled to electric motor 202 through a coupler 195. A driven gear 197 of hydraulic pump 201 is engaged to driver gear 196. Manifold 190 includes all hydraulic passages. Reservoir 230 includes an air/fluid divider 236 and an air valve 237. Air valve 237 allows for pressurizing the air in reservoir 230. A heat sink 192 allows for heat transfer from electric motor 202. Pressure sensors 126 and 127 measure the hydraulic pressure in two chambers of the torque generator 104. A rod end 106 connects torque generator 104 to thigh link 103. Components labeled 191 and 235 are a motor mounting plate and a reservoir housing, respectively.

Figure 26:
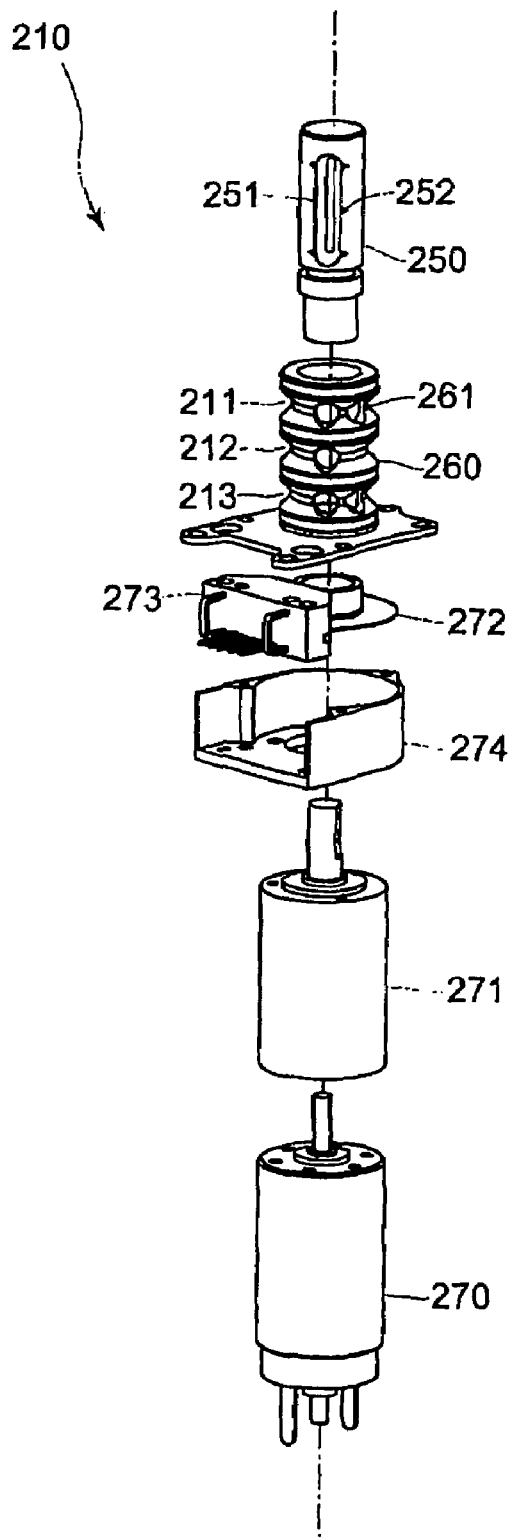
FIG. 26 is an exploded view of the three-way valve of FIG. 25.
Figure 27:
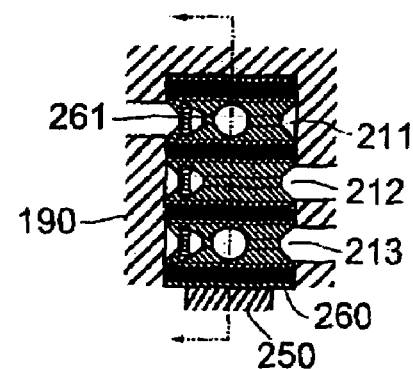
FIG. 27 is a partial cross-sectional side view of the three-way valve of FIG. 26 in a first position.
Figure 28:
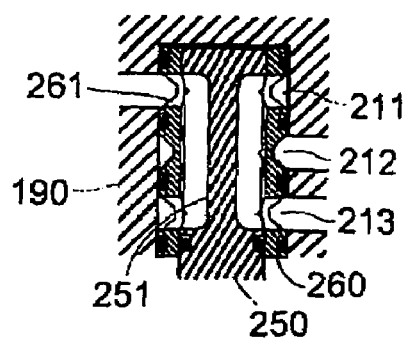
FIG. 28 is a partial cross-sectional side view of the three-way valve of FIG. 26 in a second position.
Figure 29A:
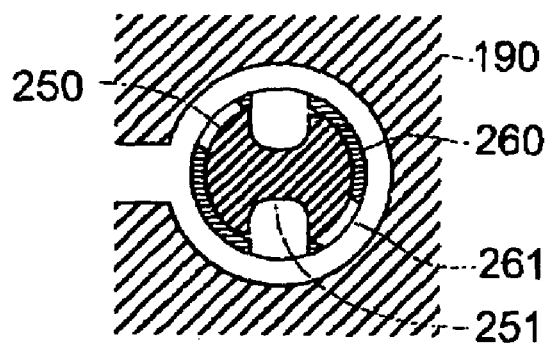
FIG. 29A is a partial cross-sectional top view of the three-way valve of FIG. 26 in a first position.
Figure 29B:
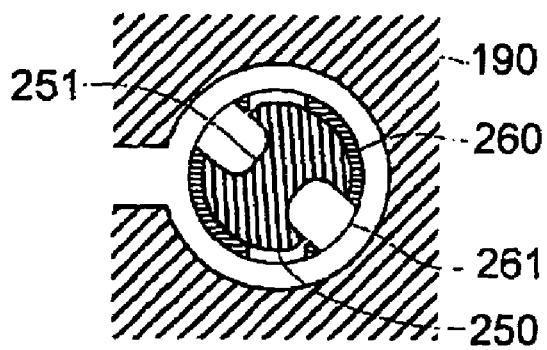
FIG. 29B is a partial cross-sectional top view of the three-way valve of FIG. 26 in a second position.
Figure 29C:
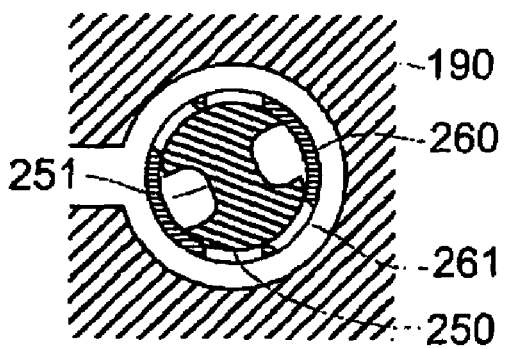
FIG. 29C is a partial cross-sectional top view of the three-way valve of FIG. 26 in a third position.
Figure 29D:
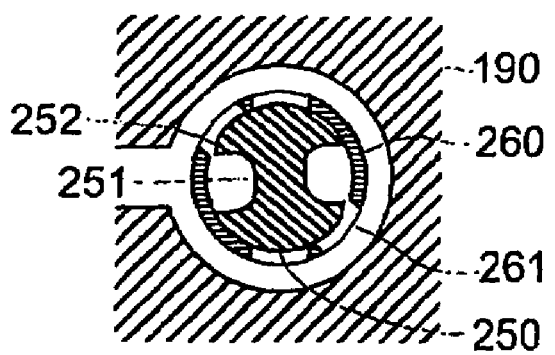
FIG. 29D is a partial cross-sectional top view of the three-way valve of FIG. 26 in a fourth position.

FIG. 26 describes the details of three-way valve 210. A valve electric motor 270 is coupled to a valve transmission 271. An encoder, which includes an encoder housing 274, an encoder disk 272 and an encoder read head 273, measures the valve position. A valve housing 260 has three ports 211, 212, and 213. In this embodiment, there are five orifices 261 in valve housing 260. A valve barrel 250 is coupled to valve transmission 271 output shaft. Two slots 251 are created in valve barrel 250 as shown in FIGS. 26 and 28. As valve barrel 250 is turned by valve electric motor 270, three-way valve 210 assumes one of at least three positions described by FIG. 16. As shown in FIG. 29A, when three-way valve 210 is in its first position, port 211 and port 213 are fully open to each other. When three-way valve 210 is in its second position (FIG. 29B), port 211, port 212 and port 213 are connected. When three-way valve 210 is in its third position (FIG. 29C), no ports are connected. As can be seen from FIG. 26 and FIG. 29D there are some notches 252 on slot 251 that allow for controllable openings of the ports. Needless to say, valve barrel 250 can be in other positions besides positions depicted in FIG. 29A-D. To obtain the desired resistance to fluid flow, the valve can be adjusted by signal processor in real time to achieve optimal performance.

Figure 30:
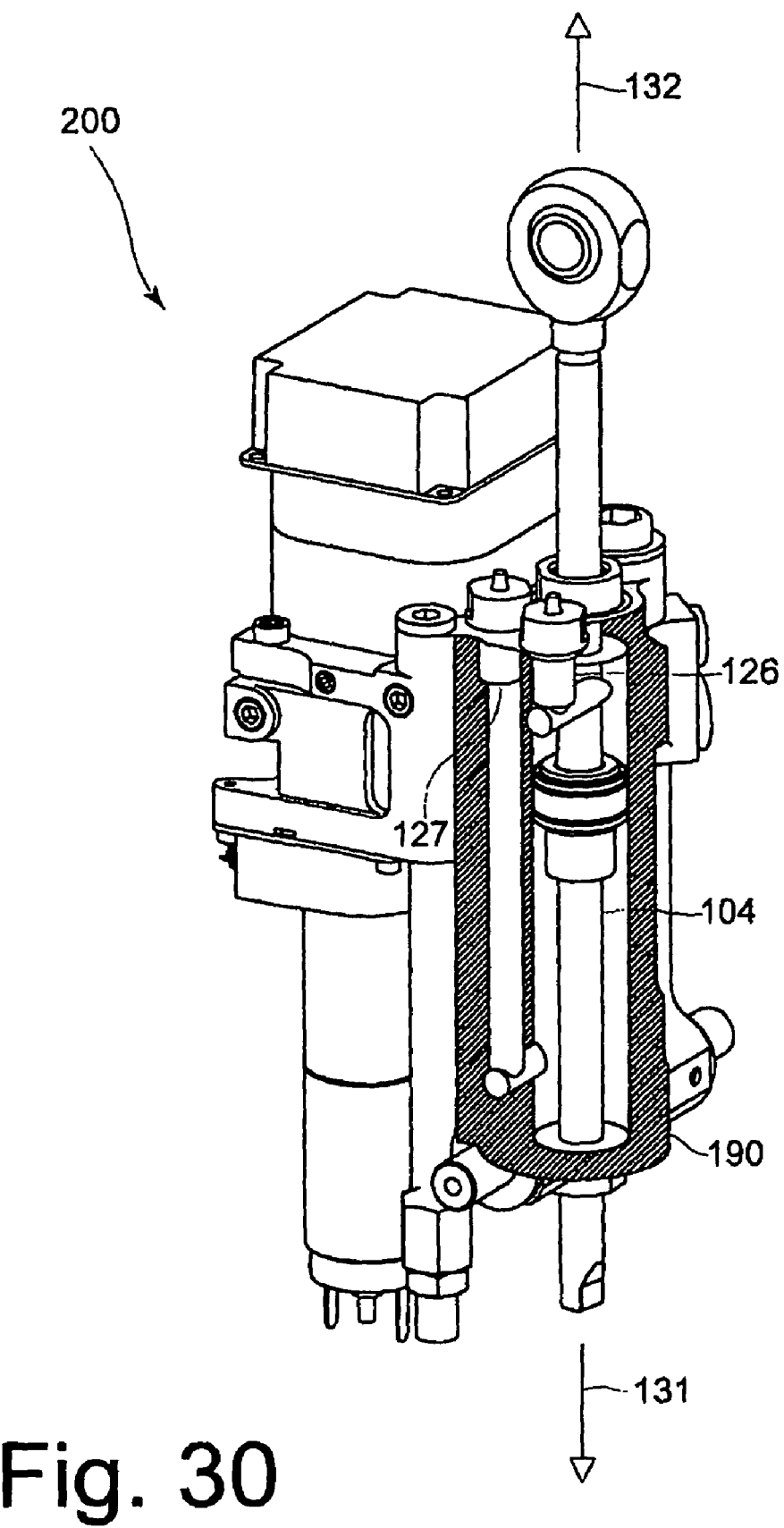
FIG. 30 is a partial cross-sectional view of a hydraulic power circuit of the present invention.

FIG. 30 represents an embodiment of semi-actuated prosthetic knee 100 where pressure sensors 126 and 127 measure the hydraulic pressure on both sides of torque generator 104. Additionally, FIG. 30 represents an embodiment of hydraulic power unit 200 where hydraulic manifold 190 is shown cut away so that connection paths between torque generator 104 and pressure sensors 126 and 127 are visible.

Figure 31:
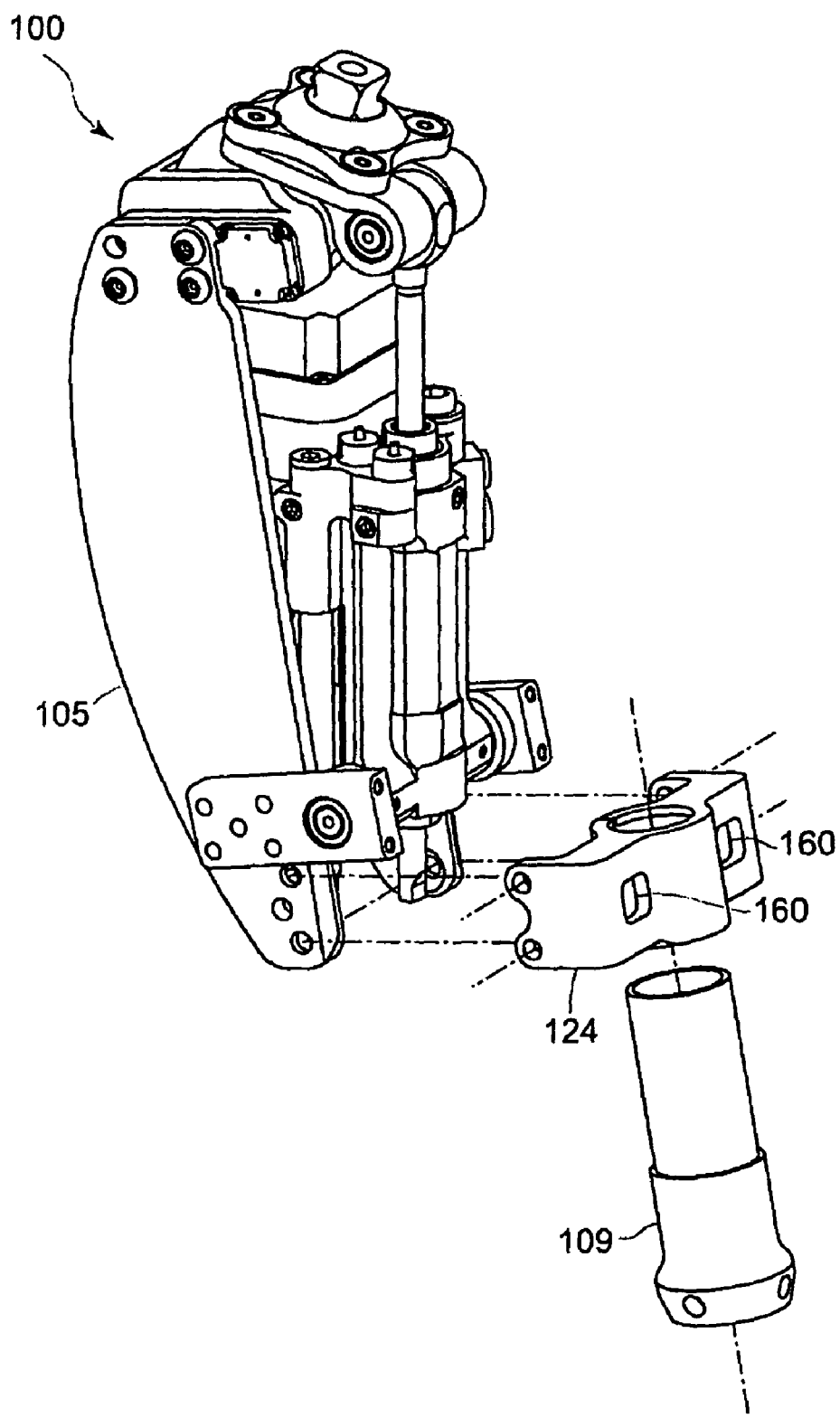
FIG. 31 is a partial exploded view of the semi-actuated knee of FIG. 20.
Figure 32A:
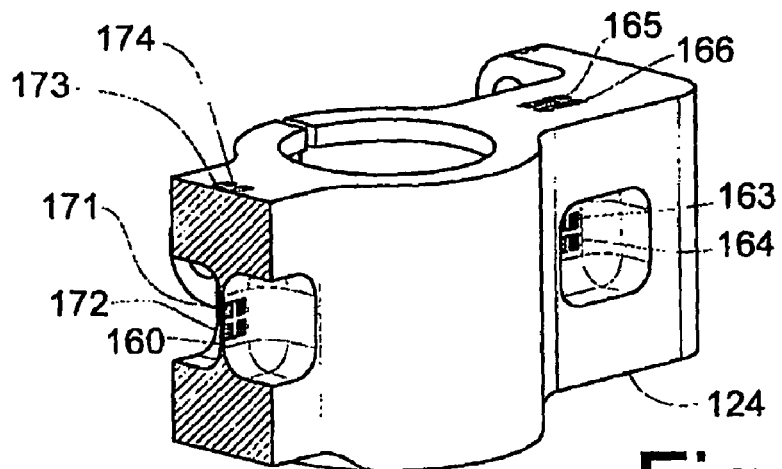
FIG. 32A is a partial cross-sectional back perspective view of a stance sensor of the present invention.
Figure 32B:
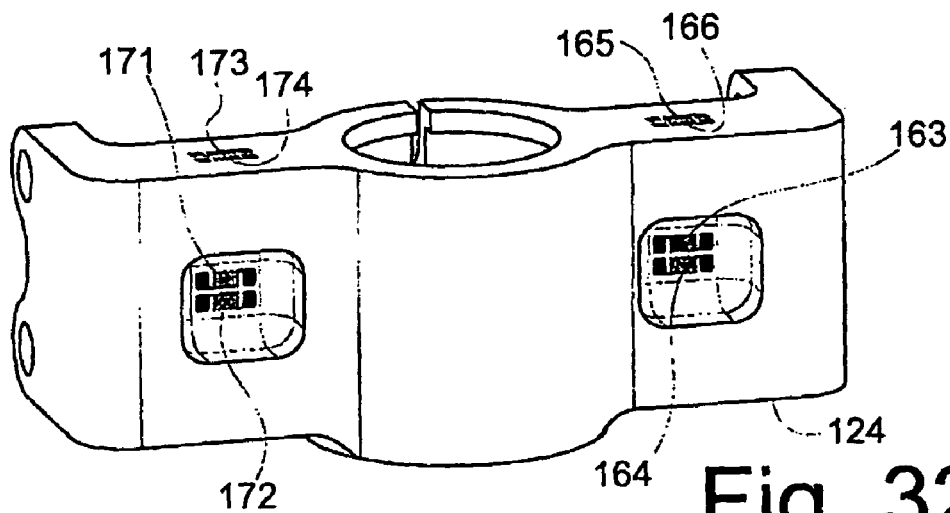
FIG. 32B is a back perspective view of the stance sensor of FIG. 32A.
Figure 32C:
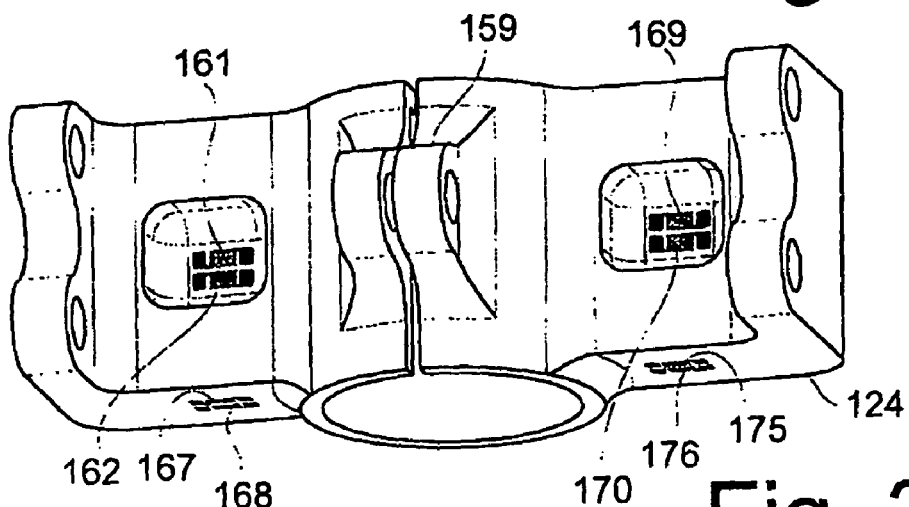
FIG. 32C is a front perspective view of the stance sensor of FIG. 32A.

FIG. 31 shows the implementation of stance sensor 124 in the embodiment of semi-actuated knee 100 shown in FIG. 20. Stance sensor 124 connects ankle pylon 109 to shank link 105. In this embodiment, stance sensor 124 is instrumented with several strain gages 161-172 to measure forces and moments transmitted through shank link 105 during stance phase. FIGS. 32A-32C shows the locations of strain gages 161-172 on stance sensor 124. Stance sensor 124 comprises a tube clamp 159 as depicted in FIG. 32C that clamps to ankle pylon 109.

Strain gages 161, 162, 163, 164 are electrically connected in a wheatstone bridge configuration to measure the vertical shear strains in a shear web 160 due to vertical forces on one of the webs. Strain gages 169, 170, 171, 172 are electrically connected in a wheatstone bridge configuration to measure the vertical shear strain in the second shear web. Summing the vertical shear measurements from both webs 160 cancels out frontal plane moments which might contaminate the vertical shear measurements. Strain gages 165, 166, 167, 168 are electrically connected in a wheatstone bridge configuration to measure the shear strains due to sagittal plane moment loads on the right side of stance sensor 124. Strain gages 173, 174, 175, 176 are electrically connected in a wheatstone bridge configuration to measure the shear strains due to sagittal plane moment loads on the left side of stance sensor 124. Summing the moment load measurements from the left and right sides of stance sensor. 124 cancels out rotational moments which might contaminate the sagittal moment measurements. Since rotational moments on stance sensor 124 are small in normal operation in comparison with sagittal plane moments, strain gages 165, 166, 167, 168 or strain gages 173, 174, 175, 176 may be electrically connected in an alternative wheatstone bridge configuration to measure horizontal shear strains due to horizontal forces on the right or left side of stance sensor 124.

Figure 33:
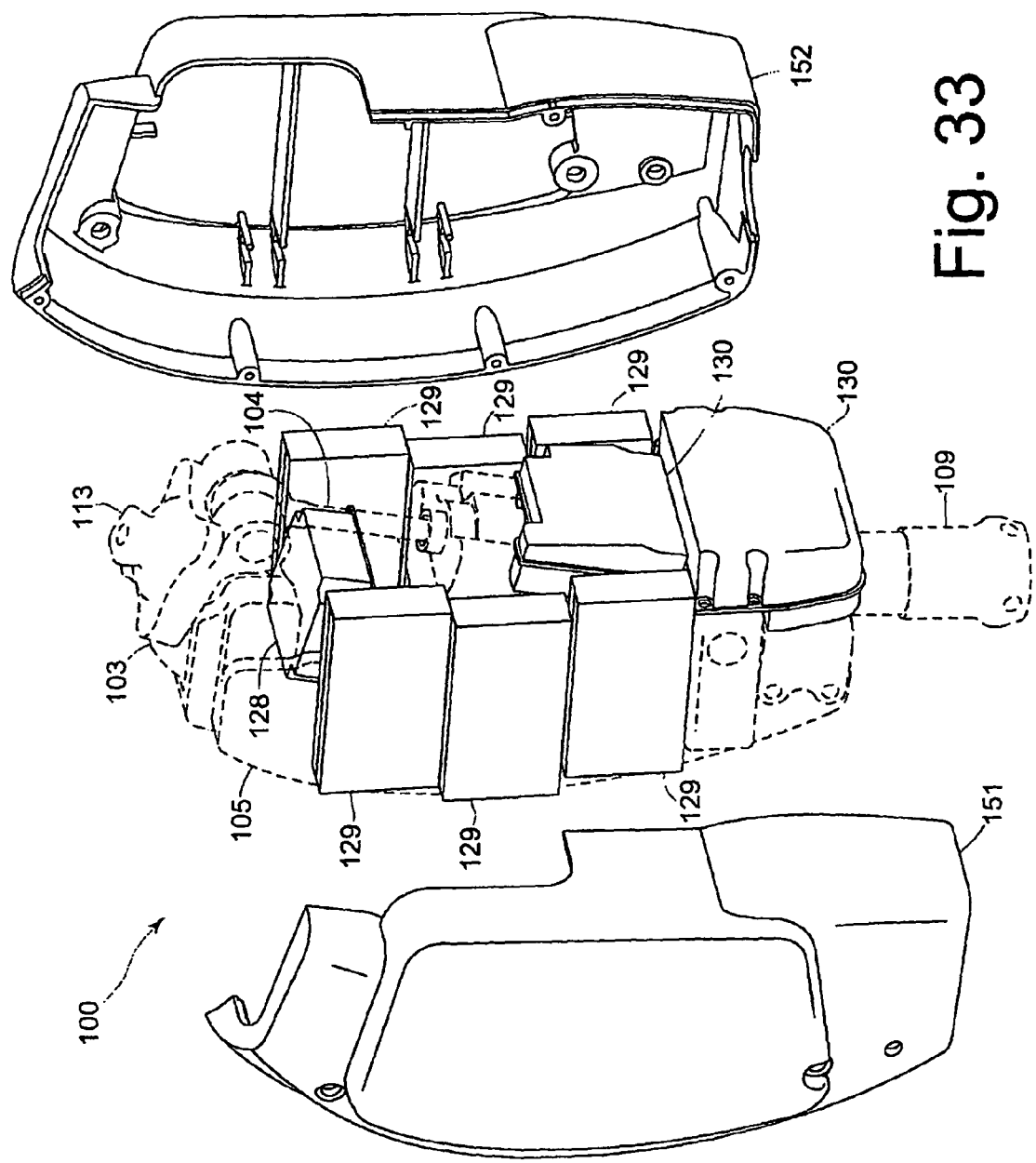
FIG. 33 is a partial exploded view of a semi-actuated prosthetic knee of the present invention.

FIG. 33 shows semi-actuated prosthetic knee 100 where covers 151 and 152 are removed.

Figure 34:
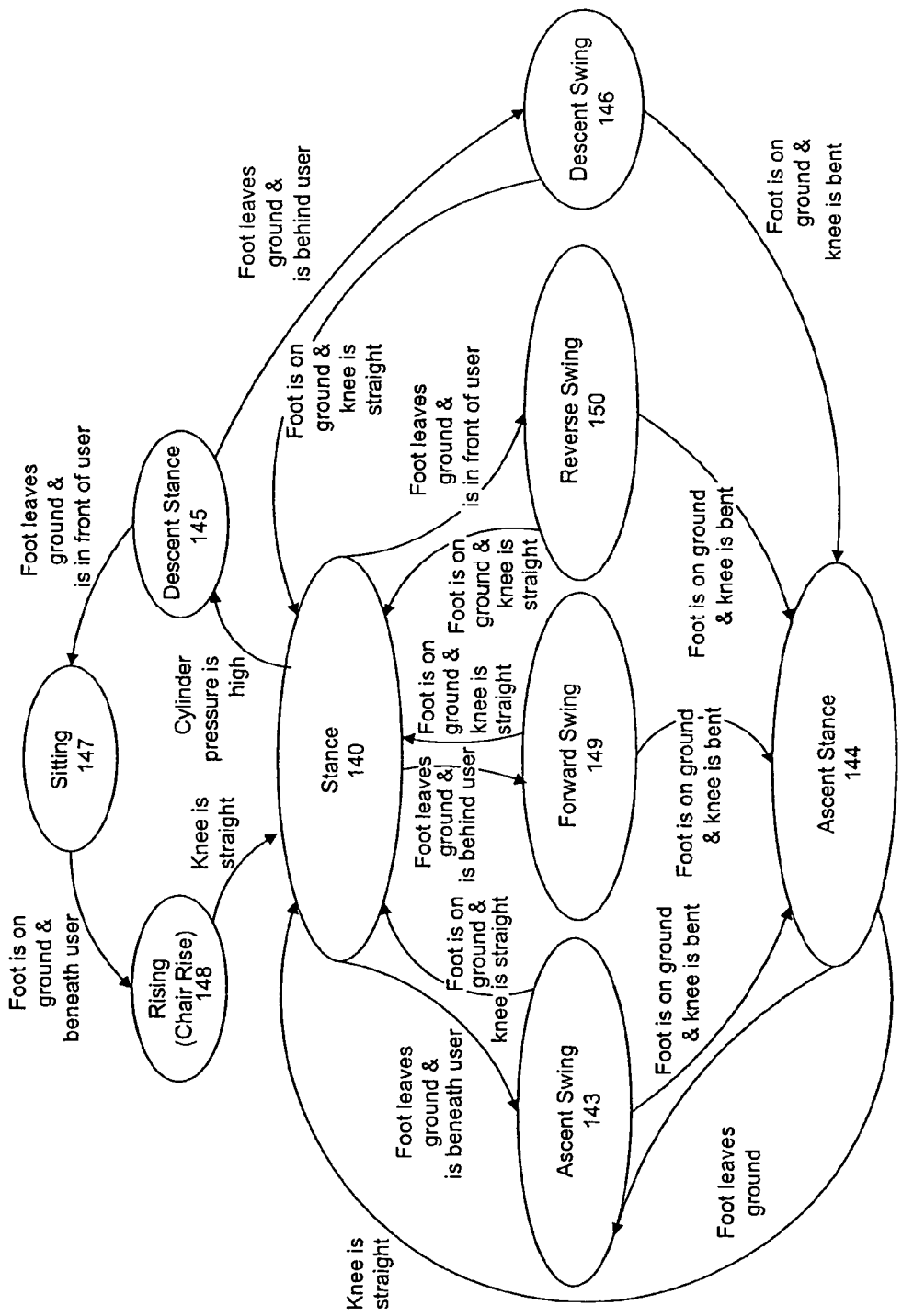
FIG. 34 is a diagram of states implemented by a signal processor in accordance with the invention.

In some embodiments, signal processor 130 receives information from various sensors and implements various controllers onto the knee. These controllers are referred to as "states" in this document. FIG. 34 is a diagram of states implemented by signal processor 130. All states are labeled. The arrows show the conditions under which signal processor 130 moves the prosthetic knee from one state to another. Below the states and the conditions to move-to that state is described.

Stance

In operation, signal processor 130 begins to implement a stance state 140 when stance sensor 124 indicates that artificial foot 108 has contacted the ground as depicted in FIG. 20. In some embodiments of the invention, during a portion of stance state 140, semi-actuated prosthetic knee 100 operates in the un-actuated mode. This means that during this portion of stance state 140 where semi-actuated prosthetic knee 100 operates in the un-actuated mode, semi-actuated prosthetic knee 100 is configured such that no electric power from electric power source 205 is transferred to electric motor 202 and hydraulic valve circuit 204 modulates the resistance of the fluid flow in torque generator 104. The ability to modulate the resistance of fluid flow in torque generator 104 allows one to control the resistance of knee mechanism 107 to forces and torques during a portion of stance state 140, which reduced use of electric power since electric motor 202 is not consuming any electric power in this un-actuated mode.

In some embodiments of the invention when stance sensor 124 indicates that the heel of artificial foot 108 is taking more load than the toe of artificial foot 108, hydraulic power unit 200 imposes a greater resistance to fluid flow in torque generator 104 than of when stance sensor 124 indicates that the toe of artificial foot 108 is taking more load than the heel of artificial foot 108.

Forward Swing

In some embodiments of the invention, signal processor 130 begins to implement a forward swing state 149 when semi-actuated prosthetic knee 100 is operating in stance state 140 and signal processor 130 learns that artificial foot 108 has separated from the ground generally behind the amputee's trunk. In some embodiments of the invention, during a portion of forward swing state 149, semi-actuated prosthetic knee 100 operates in the actuated mode. This means during this portion of forward swing 149 where semi-actuated prosthetic knee 100 operates in the actuated mode, semi-actuated prosthetic knee 100 is configured such that it transfers electric power from electric power source 205 to electric motor 202 powering electric motor 202 and hydraulic pump 201. In this actuated mode, hydraulic valve circuit 204 is configured such that hydraulic pump 201 hydraulically couples to torque generator 104 such that the entire hydraulic pump output flow travels to torque generator 104. This hydraulic coupling between hydraulic pump 201 and torque generator 104 allows signal processor 130 to control torque generator 104 directly by controlling electric motor 202. The ability to inject power to torque generator 104 allows one to control the motion of knee mechanism 107 or impose desirable torque onto knee mechanism 107 during a portion or entire forward swing state 149.

In some embodiments of the invention, during a portion of forward swing state 149, signal processor 130 controls the angle between thigh link 103 and shank link 105 such that artificial foot 108 follows a trajectory. In some other embodiments of the invention, during a portion of forward swing state where prosthetic knee 100 operates in the actuated mode, signal processor 130 controls the angle between thigh link 103 and shank link 105 as a function of thigh angle signal 156 (depicted in FIG. 1) such that artificial foot 108 follows a trajectory. This allows the amputee to move artificial foot 108 forward and backward (i.e. change direction) during swing and have artificial foot 108 on a trajectory. In some embodiments, the trajectory for artificial foot 108 is a straight line generally parallel to the ground. It should be understood that one can use a shank angle sensor in conjunction with knee angle sensor 120 to arrive at thigh angle signal 156. In more detailed embodiment of the invention, during a portion of forward swing state 149 where prosthetic knee 100 operates in the actuated mode, signal processor 130 controls the angle between thigh link 103 and shank link 105 first as a function of thigh angle signal 156 and then as a function of time. For example in some embodiments, after regulating artificial foot 108 on a trajectory up to a point that artificial foot 108 is in front of the amputee's body, signal processor 130 extends the knee in a time suitable for the current walking speed. In some other embodiments of the invention, during a portion of forward swing state 149 where prosthetic knee 100 operates in the actuated mode, signal processor 130 controls the angle between thigh link 103 and shank link 105 such that the absolute angle of shank link 105 follows a trajectory.

Reverse Swing

In some embodiments of the invention, signal processor 130 begins to implement a reverse swing state 150 when semi-actuated prosthetic knee 100 is operating in stance state 140 and signal processor 130 learns that artificial foot 108 has separated from the ground in front of the amputee's trunk. In some embodiments of the invention, during a portion of reverse swing state 150, semi-actuated prosthetic knee 100 operates in the actuated mode.

This means that during this portion of reverse swing, the ability to inject power to torque generator 104 allows one to control the motion of knee mechanism 107 or impose desirable torque onto knee mechanism 107 during a portion or entire reverse swing state 150.

In some embodiments of the invention, during a portion of reverse swing state 150, signal processor 130 controls the angle between thigh link 103 and shank link 105 such that artificial foot 108 follows a trajectory. In some other embodiments of the invention, during a portion of reverse swing state 150 where semi-actuated prosthetic knee 100 operates in the actuated mode, signal processor 130 controls the angle between thigh link 103 and shank link 105 as a function of thigh angle signal 156 such that artificial foot 108 follows a trajectory. This allows the amputee to move artificial foot 108 forward and backward (i.e. change direction) during reverse swing 150 and have artificial foot 108 on a trajectory. In some embodiments, the trajectory for artificial foot 108 is a straight line generally parallel to the ground. Again, it should be understood that one can use a shank angle sensor in conjunction with knee angle sensor 120 to arrive at thigh angle signal 156. In a more detailed embodiment of the invention, during a portion of reverse swing state 150 where prosthetic knee 100 operates in the actuated mode, signal processor 130 controls the angle between thigh link 103 and shank link 105 first as a function of thigh angle signal 156 and then as a function of time. For example in some embodiments, after regulating artificial foot 108 on a trajectory up to a point that artificial foot 108 is behind the amputee's body, signal processor 130 extends the knee in a time suitable for walking backwards. In some other embodiments of the invention, during a portion of reverse swing state 150 where prosthetic knee 100 operates in the actuated mode, signal processor 130 controls the angle between thigh link 103 and shank link 105 such that the absolute angle of shank link 105 follows a trajectory.

Ascent Swing

In some embodiments of the invention, signal processor 130 begins to implement an ascent swing state 143 when semi-actuated prosthetic knee 100 is operating in stance state 140 and signal processor 130 learns that said artificial foot 108 just separated from the ground generally beneath the amputee's trunk. In some embodiments of the invention, during a portion of ascent swing state 143, semi-actuated prosthetic knee 100 operates in the actuated mode. This means during this portion of ascent swing state 143 where semi-actuated prosthetic knee 100 operates in the actuated mode prosthetic knee 100 is configured such that it transfers electric power from electric power source 205 to electric motor 202 turning electric motor 202 and hydraulic pump 201.

In some embodiments of the invention, during a portion of ascent swing state 143, signal processor 130 controls the angle between thigh link 103 and shank link 105 such that artificial foot 108 follows a trajectory. In some other embodiments of the invention, during a portion of ascent swing state signal processor 130 controls the angle between thigh link 103 and shank link 105 as a function of thigh angle signal 156 such that artificial foot 108 follows an arbitrary trajectory. This allows the amputee to move artificial foot 108 up and down (i.e. change direction) during ascent swing and have artificial foot 108 on a trajectory. In some embodiments, the trajectory for artificial foot 108 is a path that moves up and then forward in order to place the artificial foot on top of a stair step. Again, it should be understood that one can use a shank angle sensor in conjunction with knee angle sensor 120 to arrive at thigh angle signal 156. In some other embodiments of the invention, during a portion of ascent swing state 143 where prosthetic knee 100 operates in the actuated mode, signal processor 130 controls the angle between thigh link 103 and shank link 105 such that the absolute angle of shank link 105 follows a trajectory or maintains a constant value.

Ascent Stance

In some embodiments of the invention, signal processor 130 begins to implement an ascent stance state 144 when stance sensor 124 indicates that artificial foot 108 has contacted the ground with the knee angle substantially bent. During a portion of this ascent stance state 144, semi-actuated prosthetic knee 100 operates in the actuated mode.

In some embodiments of the invention, during a portion of ascent stance state 144, signal processor 130 controls the angle between thigh link 103 and shank link 105 such that the knee angle follows a trajectory. In some other embodiments of the invention, during a portion of ascent stance state 144, signal processor 130 controls the torque generated by torque generator 104. In some further embodiments of the invention, during a portion of ascent stance state 144, signal processor 130 controls the current to electric motor 202. In some other embodiments of the invention, during a portion of ascent stance state 144, signal processor 130 controls the speed of electric motor 202.

In some embodiments of the invention, signal processor 130 begins to implement an ascent swing state 143 when semi-actuated prosthetic knee 100 is operating in ascent stance state 144 and signal processor 130 learns that said artificial foot 108 just separated from the ground (regardless of the position of the foot). Signal processor 130 begins to implement a stance state 140 when semi-actuated prosthetic knee 100 is operating in ascent stance state 144 and knee angle signal 155 indicates that semi-actuated prosthetic knee 100 is not bent.

Descent Stance

In some embodiments of the invention, signal processor 130 begins to implement a descent stance state 145 when semi-actuated prosthetic knee 100 is operating in stance state 140 and the torque in torque generator 104 is larger than a particular value. During descent stance state 145, the user intends to bend semi-actuated prosthetic knee 100 and that causes an increase in the torque of torque generator 104. In one embodiment, pressure sensors 126 and 127 are used to measure the force in torque generator 104, thereby reflecting the torque associated in torque generator 104. In some embodiments of the invention, signal processor 130 begins to implement a descent stance state 145 when semi-actuated prosthetic knee 100 is operating in stance state 140 and pressure sensors 126 and 127 indicate high pressure difference between first and second torque generator chambers. In some embodiments of the invention, during a portion of descent stance state 145, semi-actuated prosthetic knee 100 operates in the un-actuated mode.

This means during this portion of descent stance state 145 where semi-actuated prosthetic knee 100 operates in the un-actuated mode, semi-actuated prosthetic knee 100 is configured such that no electric power from electric power source 205 is transferred to electric motor 202 and hydraulic valve circuit 204 modulates the resistance of the fluid flow in torque generator 104. The ability to modulate the resistance of fluid flow in torque generator 104 allows one to control the resistance of knee mechanism 107 to forces and torques during a portion of descent stance state 145 with reduced use of electric power since electric motor 202 is not consuming any electric power in this un-actuated mode.

In some embodiments the semi-actuated prosthetic knee 100 includes a power regenerative mode, which is used during descent stance state 145. In this mode, pump valve 203 is not closed allowing at least a portion of the hydraulic flow from torque generator 104 to turn hydraulic pump 201 and the motor controller forces electric motor 202 to generate electric power. This could be accomplished in a number of ways which are not hydraulic as well.

Descent Swing

In some embodiments of the invention, signal processor 130 begins to implement a descent swing state 146 when signal processor 130 learns that during descent stance state 145 artificial foot 108 just separated from the ground and is positioned behind the amputee's trunk. In some embodiments of the invention, during a portion of descent swing state 145, semi-actuated prosthetic knee 100 operates in the actuated mode.

In some embodiments of the invention, during a portion of descent swing state 145, signal processor 130 controls the angle between thigh link 103 and shank link 105 such that artificial foot 108 follows a trajectory. In some other embodiments of the invention, during a portion of ascent swing state signal processor 130 controls the angle between thigh link 103 and shank link 105 as a function of thigh angle signal 156 such that artificial foot 108 follows a trajectory. In a more detailed embodiment of the invention, during a portion of descent swing state 146 where prosthetic knee 100 operates in the actuated mode, signal processor 130 controls the angle between thigh link 103 and shank link 105 first as a function of thigh angle signal 156 and then as a function of time. For example in some embodiments, after regulating artificial foot 108 on a trajectory up to a point that artificial foot 108 is estimated to have cleared a standard stair, signal processor 130 extends the knee in a time suitable for walking down stairs. In some other embodiments of the invention, during a portion of descent swing state 146 where prosthetic knee 100 operates in the actuated mode, signal processor 130 controls the absolute angle of shank link 105 to follow an arbitrary trajectory.

Sitting

In some embodiments of the invention, signal processor 130 begins to implement a sitting state 147 when signal processor 130 learns that during descent stance state 145 artificial foot 108 just separated from the ground in front of the amputee's trunk. In some embodiments of the invention, during a portion of sitting state 147, semi-actuated prosthetic knee 100 operates in the un-actuated mode. This means during this portion of sitting state 147 where semi-actuated prosthetic knee 100 operates in the un-actuated mode, semi-actuated prosthetic knee 100 is configured such that no electric power from electric power source 205 is transferred to electric motor 202 and hydraulic valve circuit 204 modulates the resistance of the fluid flow in torque generator 104 so prosthetic knee 100 flexes smoothly with little or no resistance. The ability to modulate the resistance of fluid flow in torque generator 104, allows one to control the resistance of knee mechanism 107 to forces and torques during a portion of stance state 140 with reduced use of electric power since electric motor 202 is not consuming any electric power in this un-actuated mode.

Rising (Chair Rise)

In some embodiments of the invention, signal processor 130 begins to implement a rising state 148 when stance sensor 124 indicates that, during sitting state 147, artificial foot 108 has contacted the ground beneath the amputee. During a portion of this rising state 148 semi-actuated prosthetic knee 100 operates in the actuated mode. In some embodiments of the invention, during a portion of rise state 148, signal processor 130 controls the angle between thigh link 103 and shank link 105 such that the knee angle follows a trajectory. In some other embodiments of the invention, during a portion of rise state 148, signal processor 130 controls the torque generated by torque generator 104. In some further embodiments of the invention, during a portion of rise state 148, signal processor 130 controls the current to electric motor 202. In some other embodiments of the invention, during a portion of rise state 148, signal processor 130 controls the speed of electric motor 202.

Figure 35:
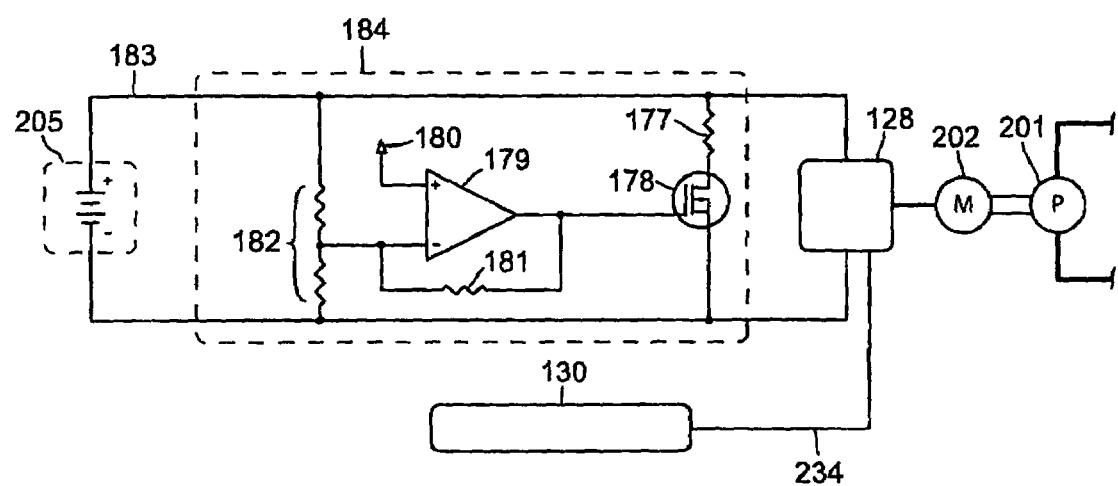
FIG. 35 is an electrical schematic showing the connection of an electric power source to a motor controller.

FIG. 35 is an electrical schematic showing the connection of electric power source 205 to motor controller 128, including an overcharge protection circuit 184. In power regenerative mode, hydraulic fluid flows through hydraulic pump 201, which causes electric motor 202 to turn and generate electricity. The signal processor 130, commands a desired current to the motor controller 128, which increases the voltage of a bus 183 such that energy flows from the electric motor 202 into the power source 205, thus regenerating power. If the bus voltage becomes sufficiently high, a voltage divider 182 causes a comparator 179 to turn on a switch 178 which diverts regenerating current away from power source 205 and instead dissipates a fraction of the energy in a power resistor 177. A voltage reference 180 sets the trip point for the comparator 179 and a feedback resistor 181 provides hysteresis.

Although described with reference to preferred embodiments of the invention, it should be understood that various changes and/or modifications can be made to the invention without departing from the spirit thereof. In general, the invention should only be limited by the scope of the claims.

The invention claimed is:

1. A prosthetic knee device, configured to be coupled to an above-knee remaining lower limb of an amputee having a trunk, comprising:
   an artificial foot having a toe and a heel;
   a shank link coupled to the artificial foot;
   a thigh link configured to be attached to an above-knee remaining lower limb of an amputee;
   a knee mechanism interconnecting said thigh link and said shank link, said knee mechanism allowing flexion and extension movements of said thigh link and said shank link relative to each other;
   a torque generator configured to generate torque between said shank link and said thigh link;
   a knee angle sensor creating a knee angle signal representing an angle between said shank link and said thigh link;
   a stance sensor identifying which part of said artificial foot is in contact with ground;
   a power source providing electric power; and
   a signal processor connected to the power source, the torque generator and each of the knee angle and stance sensors, wherein said signal processor receives signals from the knee and stance sensors, determines an estimated location of the artificial foot with respect to the trunk of the amputee and, based on said estimated location when said artificial foot leaves the ground, selects a type of swing state from: a forward swing state; a combination forward and descent swing state; a combination forward and ascent swing state; a reverse swing state; a combination reverse and descent swing state; and a combination reverse and ascent swing state.

2. The device of claim 1 wherein said signal processor begins to implement a stance state when said stance sensor indicates that said artificial foot has contacted the ground.

3. The device of claim 2 wherein, during a portion of said stance state, said prosthetic knee is configured to operate in an un-actuated mode wherein the prosthetic knee device operates without any transfer of electric power from said electric power source to said torque generator.

4. The device of claim 2 wherein, during a portion of said stance state, said prosthetic knee is configured to resist flexion.

5. The device of claim 2 wherein, during a portion of said stance state, said signal processor causes resistance in the knee mechanism through said torque generator.

6. The device of claim 2 wherein, when said stance sensor indicates that the heel of said artificial foot is taking more load than the toe of said artificial foot, said signal processor signals for a greater resistance through said torque generator than when said stance sensor indicates that the toe of said artificial foot is taking more load than the heel of said artificial foot.

7. The device of claim 1 wherein said signal processor begins to implement the forward swing state when said artificial foot leaves the ground generally behind at least a portion of the trunk of the amputee.

8. The device of claim 7 wherein, during a portion of said forward swing state, said signal processor controls the angle between said shank link and said thigh link such that said artificial foot follows a predetermined trajectory.

9. The device of claim 7 wherein, during a portion of said forward swing state, said signal processor controls the angle between said shank link and said thigh link as a function of a thigh angle signal from a thigh angle sensor such that said artificial foot follows a predetermined trajectory.

10. The device of claim 1 wherein said signal processor initiates the reverse swing state when said artificial foot leaves the ground in front of the trunk of the amputee.

11. The device of claim 10 wherein, during a portion of said reverse swing state, said signal processor controls the angle between said shank link and said thigh link as a function of a thigh angle signal from a thigh angle sensor such that said artificial foot follows a predetermined trajectory.

12. The device of claim 10 wherein, during a portion of said reverse swing state, said signal processor controls the angle between said shank link and said thigh link such that said artificial foot follows a predetermined trajectory.

13. The device of claim 1 wherein said signal processor begins to implement the ascent swing state when said artificial foot leaves the ground generally beneath the trunk of the amputee.

14. The device of claim 13 wherein, during a portion of said ascent swing state, said signal processor controls the angle between said shank link and said thigh link.

15. The device of claim 14 wherein, during the portion of said ascent swing state, said signal processor controls the angle between said shank link and said thigh link as a function of a thigh angle signal from a thigh angle sensor such that said artificial foot follows a predetermined trajectory.

16. The device of claim 1 wherein said signal processor begins to implement an ascent stance state when said stance sensor indicates that said artificial foot contacted the ground with a substantially bent knee angle.

17. The device of claim 16 wherein, during a portion of said ascent stance state, said signal processor controls the angle between said shank link and said thigh link.

18. The device of claim 16 wherein, during a portion of said ascent stance state, said signal processor controls torque generated by said torque generator.

19. The device of claim 16 wherein, during a portion of said ascent stance state, said signal processor controls a speed of said torque generator.

20. The device of claim 1 wherein the torque generator includes multiple chambers and the device further comprises: a pressure sensor for the torque generator, wherein said signal processor implements a descent stance state when said artificial foot is in contact with the ground and said pressure sensor indicates a large pressure difference between the multiple chambers of said torque generator.

21. The device of claim 20 wherein, during a portion of said descent stance state, said prosthetic knee is configured to operate in an un-actuated mode wherein the prosthetic knee device operates without any transfer of electric power from said electric power source to said torque generator.

22. The device of claim 20 wherein, during a portion of said descent stance state, said prosthetic knee is configured to resist flexion.

23. The device of claim 1, wherein said signal processor begins to implement the descent swing state when said stance sensor indicates that said artificial foot leaves the ground behind the trunk of the amputee.

24. The device of claim 23 wherein, during a portion of said descent swing state, said signal processor controls the angle between said shank link and said thigh link.

25. The device of claim 24 wherein, during the portion of said descent swing state, said signal processor controls the angle between said shank link and said thigh link as a function of a thigh angle signal from a thigh angle sensor such that said artificial foot follows a predetermined trajectory.

26. The device of claim 1 wherein said signal processor implements a sitting state when said signal processor learns that, during said descent stance state, said artificial foot just separated from the ground and is positioned in front of the trunk of the amputee.

27. The device of claim 26 wherein, during a portion of said sitting state, said prosthetic knee is configured to operate in an un-actuated mode wherein the prosthetic knee device operates without any transfer of electric power from said electric power source to said torque generator.

28. The device of claim 26 wherein, during a portion of said sitting state, said prosthetic knee is configured to flex smoothly with little or no resistance.

29. The device of claim 1 wherein said signal processor begins to implement a rising state when, during a sitting state, said stance sensor indicates that said artificial foot is contacting the ground generally beneath the trunk of the amputee.

30. The device of claim 29 wherein, during a portion of said rising state, said signal processor controls the angle between said shank link and said thigh link.

31. The device of claim 29 wherein, during a portion of said rising state, said signal processor controls an amount of torque generated by said torque generator.

32. The device of claim 29 wherein, during a portion of said rising stance state, said signal processor controls a current to an electric motor coupled to said torque generator.

33. The device of claim 29 wherein, during a portion of said rising stance state, said signal processor controls a speed of said torque generator.

34. The device of claim 1, wherein said stance sensor comprises a force-torque sensor installed on said shank link measuring both force and moment in a sagittal plane.

35. The device of claim 1, further comprising a thigh angle sensor generating a thigh angle signal representing the absolute angle of said thigh link.

36. The device of claim 1, wherein the torque generator is a hydraulic torque generator, the device further comprising:
a hydraulic power unit coupled to the hydraulic torque generator, the hydraulic power unit including a hydraulic valve circuit hydraulically coupled to said torque generator, a hydraulic pump, and an electric motor mechanically coupled to said hydraulic pump, wherein the signal processor is connected to the power source and the hydraulic power unit controlling operation of the hydraulic power unit.

37. The device of claim 36, wherein said hydraulic valve circuit comprises a first controllable valve and a pump valve serially connected to each other, said hydraulic pump being coupled to said first controllable valve and to said pump valve, and said torque generator being coupled to two ports of said first controllable valve wherein, when said semi-actuated prosthetic knee operates in its actuated mode, said pump valve does not close, allowing said signal processor to control said torque generator by controlling said electric motor and, when said semi-actuated prosthetic knee operates in its un-actuated mode, said first controllable valve modulates the resistance of the fluid flow in said torque generator.

38. The device of claim 36, wherein said hydraulic valve circuit comprises a first controllable valve and an actuator valve serially connected to each other, said torque generator being coupled to said first controllable valve and said actuator valve, and said hydraulic pump is coupled to two ports of said first controllable valve wherein, when said semi-actuated prosthetic knee operates in its actuated mode, said first controllable valve is closed and said actuator valve is not closed, allowing said signal processor to control said torque generator by controlling said electric motor and, when said semi-actuated prosthetic knee operates in an un-actuated mode, said actuator valve modulates the resistance of fluid flow in said torque generator.

39. The device of claim 36, wherein the hydraulic valve circuit further includes a first check valve installed in series with a first controllable valve coupled to the torque generator, allowing said first controllable valve to modulate resistance of fluid flow in the torque generator in one direction only.

40. The device of claim 36, wherein said hydraulic circuit further includes a restrictor valve providing resistance to fluid flow when said torque generator is operated in an extension direction.

41. The device of claim 36, wherein said prosthetic knee device is configured operate in an actuated mode, wherein electric power is transferred from said power source to said electric motor to drive the hydraulic pump to provide working fluid to said torque generator under control of the signal processor in order to create a torque between said shank link and said thigh link and, said prosthetic knee device is also configured to operate in an un-actuated mode, wherein said hydraulic valve circuit modulates a resistance of fluid flow in said torque generator such that said semi-actuated prosthetic knee operates without any transfer of electric power from said electric power source to said electric motor.

42. The device of claim 41, wherein said hydraulic valve circuit comprises a three-way valve having first, second and third ports, said hydraulic pump being coupled to the first and second ports of said three-way valve and said torque generator being coupled to the second and third ports of said three-way valve wherein, when prosthetic knee device operates in the actuated mode, said three-way valve blocks said second port and connects said first port to said third port allowing for fluid flow between said hydraulic pump and said torque generator, and when said prosthetic knee device operates in the un-actuated mode, said three-way valve blocks said first port and modulates an opening of said third port to modulate the resistance of the fluid flow through said torque generator.

43. The device of claim 42, wherein said prosthetic knee device is operable in a power regenerative mode in which said three-way valve connects said first port to said third port allowing at least a portion of the fluid flow from said torque generator to turn said hydraulic pump and a motor controller applies a non-zero current onto said electric motor to resist the fluid flow in said hydraulic pump.

44. The device of claim 36, wherein said hydraulic valve circuit comprises a three-way valve having first, second and third ports, said hydraulic pump being coupled to the first and second ports of said three-way valve and said torque generator being coupled to a third port and said second port wherein, when said prosthetic knee device operates in the actuated mode, said three-way valve blocks said second port and connects said-first port to said third port allowing for fluid flow between said hydraulic pump and said torque generator and, when said prosthetic knee device operates in the un-actuated mode, said three-way modulates an opening of said third port thereby modulating the resistance of the fluid flow in said torque generator.

45. The device of claim 36, further comprising two pressure sensors respectively measuring hydraulic fluid pressure in first and second chambers of said torque generator.

46. The device of claim 36, wherein said prosthetic knee device is operable in a power regenerative mode in which said hydraulic pump hydraulically couples to said torque generator and at least a portion of hydraulic flow from said torque generator flows to said hydraulic pump causing said electric motor to turn and generate electric power.

47. A prosthetic knee device, configured to be coupled to the lower limb of a person, comprising:
an artificial foot having a toe and a heel;
a shank link coupled to the artificial foot;
a thigh link configured to be attached to a person;
a knee mechanism interconnecting said thigh link and said shank link, said knee mechanism allowing flexion and extension movements of said thigh link and said shank link relative to each other;
a torque generator configured to generate torque between said shank link and said thigh link;
a knee angle sensor creating a knee angle signal representing the angle between said shank link and said thigh link;
a stance sensor configured to identify which part of said artificial foot is in contact with ground;
a power source configured to provide electric power; and
a signal processor connected to the power source, the torque generator and each of the knee angle and stance sensors, wherein said signal processor receives signals from the knee and stance sensors and, when the leg is in a swing state, controls the angle between said shank link and said thigh link through the torque generator as a function of a thigh angle signal from generated using a thigh angle sensor or calculations based on signals received from a combination of a shank angle sensor in conjunction with the knee angle sensor such that said artificial foot follows a predetermined trajectory.

48. The device of claim 47, wherein the predetermined trajectory is generally parallel to the ground.

\* \* \* \* \*